United States Patent
Kelly

Patent Number: 5,800,733
Date of Patent: Sep. 1, 1998

[54] PHOTO CROSS-LINKABLE LIQUID CRYSTAL DERIVATIVES

[75] Inventor: Stephen Kelly, Beverley, England

[73] Assignee: Rolic AG, Zug, Switzerland

[21] Appl. No.: 686,973

[22] Filed: Jul. 25, 1996

[30] Foreign Application Priority Data

Jul. 28, 1995 [CH] Switzerland ............ 02 221/95
May 9, 1996 [EP] European Pat. Off. ........... 96107341

[51] Int. Cl.$^6$ ............ C09K 19/06; C09K 19/12; C09K 19/20; C07C 69/76
[52] U.S. Cl. ............ 252/299.6; 252/299.63; 252/299.67; 252/299.01; 252/299.66; 252/299.62; 252/299.61; 544/298; 546/339; 546/342; 549/369; 549/370; 560/60; 560/65; 560/100; 560/102; 560/108
[58] Field of Search ............ 252/299.63, 299.67, 252/299.6, 299.01, 299.66, 299.62, 299.61; 544/298; 546/339, 342; 549/369, 370; 560/60, 65, 100, 102, 108

[56] References Cited

U.S. PATENT DOCUMENTS 4,983,479  1/1991  Broer et al. ............ 430/20

FOREIGN PATENT DOCUMENTS 331 233  3/1989  European Pat. Off.

*Primary Examiner*—C. H. Kelly
*Attorney, Agent, or Firm*—Bryan Cave LLP

[57] ABSTRACT

The present invention is concerned with photo cross-linkable liquid crystalline compounds in the formula

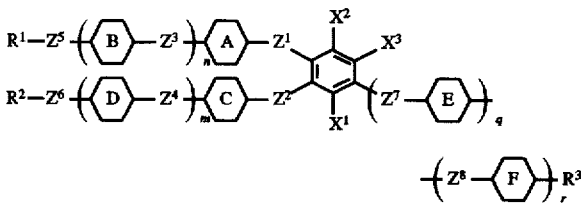

wherein for example:

A, B, C, D, E, F independently is pyridine-2,5-diyl, pyrimidine-2,5-diyl, trans-1,4-cyclohexylene, trans-1,3-dioxane-2,5-diyl $Z^1$, $Z^2$, $Z^7$ independently is —$(CH_2)_s$O—, —COO—, —$(CH_2)_s$COO—

$Z^3$, $Z^4$, $Z^8$ independently is a single bond, —$CH_2CH_2$—, —$CH_2O$—

$Z^5$, $Z^6$ independently is —$(CH_2)_s$— m, n, q and r independently is 0, 1 or 2;

s is a whole number of 1 to 16;

$R^1$, $R^2$ independently is $CH_2$=CH—COO—, $CH_2$=C($CH_3$)—COO—

$R^3$ is H, CH, COOC$_n$H$_{2n+1}$, CnH$_{2n+1}$; n=1 ... 10

$X^1$, $X^2$ and $X^3$ independently is hydrogen, halogen, cyano or lower alkyl.

The invention is also related to liquid crystalline mixtures and their use for electro-optical purpose.

19 Claims, No Drawings

PHOTO CROSS-LINKABLE LIQUID CRYSTAL DERIVATIVES

The present invention is concerned with photo cross-linkable liquid crystalline 1,2-phenylene derivatives, liquid crystalline mixtures which contain such compounds as well as their use in the cross-linked state as optical components.

Photo cross-linkable liquid crystals, which are provided with an appropriate amount of a photoinitiator, can be oriented on a substrate or in a cell by suitable orienting layers or in a field and then in this state can be cross-linked by irradiation with light of a suitable wavelength. The structure thereby produced is preserved even at high temperatures. Thus, optical components such as, for example, wave guides, optical grids and filters, piezoelectric cells and cells having non-linear optical (NLO) properties, etc. can be produced. Such optical components can be used, for example, for frequency doubling (SHG) or in colour filters.

Further properties such as, for example, the birefringence, the refractive index, the transparency, etc. must fulfil different requirements depending on the field of use. For example, materials for optical filters should have a strong absorption in a direction perpendicular to the filter surface.

In addition to the general interest in photo cross-linkable liquid crystals for optical components, such liquid crystalline materials are suitable as a cladding for glass fibres for optical data transmission. The use of such materials increases the elastic modulus in the longitudinal axis of the fibre, lessens the thermal expansion coefficients and thus reduces microdistortion losses. This leads to an increased mechanical stability.

The photo cross-linkable liquid crystals must have a good chemical and thermal stability, good solubility in usual solvents and a good stability towards electric fields and electromagnetic radiation. They should have a suitable mesophase in a temperature range from about 25° C. to about +100° C., especially from about 25° C. to about +80° C., Since liquid crystals are usually used as mixtures of several components, it is important that the components have a good miscibility with one another. Conventional photochemically oligomerisable or polymerisable liquid crystals usually have a high melting point and clearing point. This has the disadvantage that a spontaneous thermal polymerisation can occur prematurely during processing. The spontaneous thermal polymerisation can occur because the processing is carried out at temperatures barely below the clearing point, since at this temperature the viscosity in the liquid crystalline state is at its lowest and is therefore favourable for a good orientability. This spontaneous polymerisation leads to the formation of domains, by which the optical and thermal properties in the cross-linked layers which are produced can be significantly influenced. The melting point can be reduced by the production of complicated mixtures having several components, which indeed permits a processing at lower temperatures, but brings with it the danger of a crystallization of the conventional polymerisable liquid crystals. Photochemically oligomerisable or polymerisable compounds are described, for example, in EP-A-0 331 233.

There is accordingly the need, for use in optical components, optical filters, channel waveguides, Mach-Zehnder structures, homeotropic layers, etc., to produce photochemically oligomerisable or polymerisable compounds which are distinguished by an especially high optical anisotropy Dn. They should have low melting points and clearing points in order that the viscosity at normal processing temperatures in the liquid crystalline state is not too high. Further, they should be orientable and structurable as domain-free as possible and should also have an excellent thermal stability and long-term stability in the cross-linked state. Moreover, especially for channel wave guides, Mach-Zehnder structures, homeotropic layers, etc., they should have a positive dielectric anisotropy and be capable of orientation in an electric field. This permits, for example, the additional structuring by the use of electrodes of photochemically oligomerisable or polymerisable compounds which are already oriented homogeneously by an orienting layer. Conventional photochemically oligomerisable or polymerisable liquid crystals usually have a negative or a very weak positive dielectric anisotropy.

The present invention now provides compounds which are outstandingly suitable as single components or as components of liquid crystal mixtures for the aforementioned uses. The object of the present invention are compounds of formula I

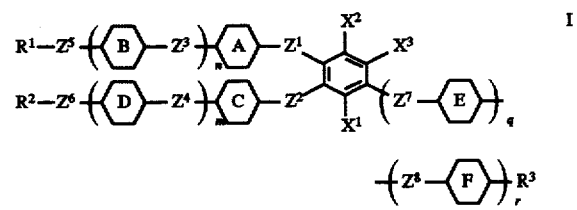

wherein each of rings A,

B, C, D, E, and F independently is pyridine-2,5-diyl, pyrimidine-2,5-diyl, trans-1,4-cyclohexylene, trans-1,3-dioxane-2,5-diyl or 1,4-phenylene which is unsubstituted or substituted with one or more of halogen, methyl or cyano;

each of $Z^1$, $Z^2$ and $Z^7$ is $-CH_2-(CH_2)_s-$, $-(CH_2)_s O-$, $-O(CH_2)_s-$, $-COO-$, $-OOC-$, $-(CH_2)_s COO-$ or $-(CH_2)_s OOC-$;

each of $Z^3$, $Z^4$ and $Z^8$ is a single bond, $-CH_2CH_2-$, $-CH_2O-$, $-OCH_2-$, $-COO-$, $-OOC-$, $-(CH_2)_4-$, $-O(CH_2)_3-$ or $-(CH_2)_3 O-$;

each of $Z^5$ and $Z^6$ is $-(CY_2)_s-$, $-O(CY_2)_s-$, $-(CY_2)_s O-$, $-(CY_2)_s COO-$, $-(CY_2)_s OOC-$, $-(Si[(CH_3)_2]O)_s-$, $-OCH_2(Si[(CH_3)_2]O)_s Si[(CH_3)_2]CH_2O-$ or $-NHCH_2(Si[(CH_3)_2]O)_s Si[(CH_3)_2]CH_2NH-$;

Y is hydrogen or fluorine;

each of m, n, q and r is 0, 1 or 2;

s is a whole number of 1 to 16;

each of $R^1$ and $R^2$ is $CH_2=CH-$, $CH_2=CH-COO-$, $CH_2=C(CH_3)-COO-$, $CH_2=C(Cl)-COO-$, $CH_2=C(Ph)-COO-$, $CH_2=CH-COO-Ph-$, $CH_2=CH-CO-NH-$, $CH_2=C(CH_3)-CONH-$, $CH_2=C(Cl)-CONH-$, $CH_2=C(Ph)-CONH-$, $CH_2=C(COOR')-CH_2-COO-$, $CH_2=CH-O-$, $CH_2=CH-OOC-$, $Ph-CH=CH-$, $CH_3-C(=NR')-$, cis, trans $HOO-CR'=CR'-COO-$,

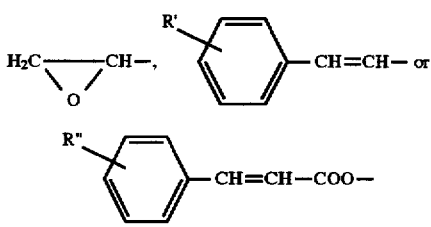

Ph is phenyl;

R' is lower alkyl;

R" is methyl, methoxy, cyano or halogen, with the proviso that $R^1$—$Z^5$ and $R^2$—$Z^6$ contain no —O—O— or —N—O— groups;

$R^3$ is hydrogen, halogen, cyano or an alkyl, alkoxy, alkoxycarbonyl or alkanoyloxy group, the alkyl methoxy, alkoxycarbonyl, or alkanoyloxy group being unsubstituted or substituted with one or more of methoxy, cyano or halogen; and each of $X^1$, $X^2$ and $X^3$ is hydrogen, halogen, cyano or lower alkyl, whereby rings B and D can be the same or different when either or both of m or n is 2.

Since the compounds of formula I in accordance with the invention or their mixtures have a mesophase, they can also, prior to the cross-linking, be oriented on an orienting layer and/or by the application of an electric or magnetic field. A uniform layer is produced in this manner.

Preferably, the cross-linkable group $R^1$ is $CH_2$=CH—COO—, $CH_2$=C($CH_3$)—COO—, $CH_2$=C(Cl)—COO—, $CH_2$=C(Ph)—COO—, $CH_2$=CH—COO—Ph—$CH_2$=CH—CONH—, $CH_2$=C($CH_3$)—CONH—, $CH_2$=C(Ph)—CONH—, $CH_2$=CH—O—, $CH_2$=CH—OOC—, 13 cis,trans —HCOO—CR'=CR'—COO—,

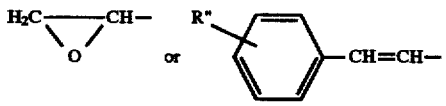

wherein R' and R" have the significance given above.

These are the residues which can be cross-linked photo-chemically after orientation of the compounds of formula I in a field.

Especially preferred groups for $R^1$ are $CH_2$=CH—COO—, $CH_2$=C($CH_3$)—COO—, $CH_2$=CH—O— and

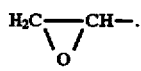

Hydrogen, fluorine, chlorine, cyano and methyl are especially preferred groups for each of $X^1$, $X^2$ and $X^3$.

As used herein, "1,4-phenylene unsubstituted or substituted with one or more of halogen, methyl or cyano" embraces in the present invention 1,4-phenylene and 1,4-phenylene mono- or multiply-substituted with fluorine, bromine, chlorine, methyl or cyano, such as, for example, 2- or 3-fluoro-1,4-phenylene, 2,3-difluoro-1,4-phenylene, 2,6- or 3,5-difluoro-1,4-phenylene, 2- or 3-chloro-1,4-phenylene, 2,3-dichloro-1,4-phenylene, 2,6- or 3,5-dichloro-1,4-phenylene, 2- or 3-bromo-1,4-phenylene, 2- or 3-methyl-1,4-phenylene, 2- or 3-cyano-1,4-phenylene and the like.

As used herein, "halogen" signifies in the scope of the present invention fluorine, chlorine or bromine, especially fluorine.

As used herein, "alkyl, alkoxy, alkoxycarbonyl or alkanoyloxy group, the alkyl, alkoxy, alkoxycarbonyl or alkanoyloxy group being unsubstituted or substituted with one or more methoxy, cyano or halogen" embraces in the scope of the present invention groups in which the alkyl residue of the aforementioned groups can be straight-chain or branched and preferably has 1 to 12 carbon atoms. The groups can be mono- or multiply-substituted with methoxy, cyano, fluorine, chlorine or bromine. Particularly preferred groups include methyl, ethyl, propyl, butyl, pentyl, methoxy, ethoxy, propyloxy, butoxy, acyloxy, propanoyloxy, butanoyloxy, methoxycarbonyl, ethoxycarbonyl, propoxycarbonyl, trifluoromethyl, trifluoromethoxy, 2,2,2-trifluoroethoxy, trifluoroacetyloxy, chlorodifluoromethoxy, 2-cyanoethyl, 2-fluoroethyl, 2-chloroethyl, 2-bromoethyl, 2-methoxyethoxy, 2,2-difluoroethyl, 2,2,2-trifluoroethyl and the like.

As used herein, "lower alkyl" embraces in the scope of the present invention straight-chain or branched residues with 1 to 5 carbon atoms such as methyl, ethyl, propyl, butyl, pentyl, i-propyl, i-butyl, t-butyl and the like.

The mesophase type of the compounds in accordance with the invention can be influenced by varying the rings in the side-chains. Thus, aromatic rings such as phenylene have the tendency to produce smectic phases, while saturated rings such as trans-1,4-cyclohexylene or trans-1,3-dioxane-2,5-diyl rings promote nematic tendencies.

Preferred compounds of the present invention are of formula I-A

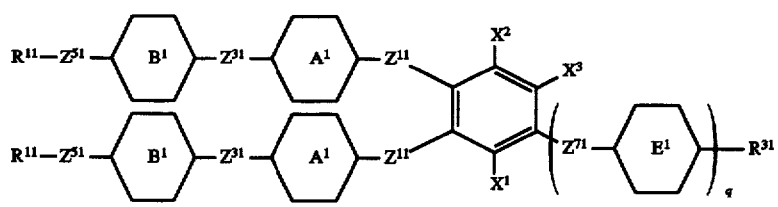

wherein each of $A^1$, $B^1$ and $E^1$ is 1,4-phenylene unsubstituted or substituted with fluorine, pyridine-2,5-diyl, pyrimidine-2,5-diyl or trans-1,4-cyclohexylene;

$Z^{11}$ is —$CH_2CH_2$—, —$CH_2O$—, —COO—, —OOC—, —$(CH_2)_4$— or —$(CH_2)_3O$—;

$Z^{31}$ is a single bond, —$CH_2O$—, —COO— or —OOC—;

$Z^{51}$ is —$(CH_2)_{s'}$—, —$(CH_2)_{s'}O$—, —$(CH_2)_{s'}COO$— or —$(CH_2)_{s'}OOC$—;

$Z^{71}$ is —$CH_2O$— or —COO—;

s' is a whole number of 3 to 12;

$R^{11}$ is $CH_2$=CH—COO—, $CH_2$=C($CH_3$)—COO—,

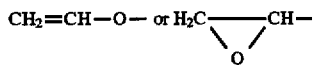

$R^{31}$ is halogen, cyano, lower alkyl or alkoxycarbonyl;

q is 0 or 1; and each of $X^1$, $X^2$ and $X^3$ have the significance given above.

Particularly preferred are compounds of formula I-A in which q is 0, such as, for example, compounds of formulae Ia–Ic wherein each of $A^2, B^2, B^3$ and $E^2$ is 1,4-phenylene unsubstituted or substituted with fluorine or trans-1,4-cyclohexylene;

$Z^{12}$ is —$(CH_2)_2COO$—, —$(CH_2)_{s'}COO$— or —$(CH_2)_{s'}O$—;

$Z^{52}$ is —$(CH_2)_{s'}$—, —$(CH_2)_{s'}O$—, —$(CH_2)_{s'}COO$— or —$(CH_2)_{s'}OOC$—;

$Z^{72}$ is —$CH_2O$— or —COO—;

s' is a whole number of 3 to 12;

$R^{12}$ is $CH_2$=CH—COO—, $CH_2$=C($CH_3$)—COO—, $CH_2$=CH—O— or

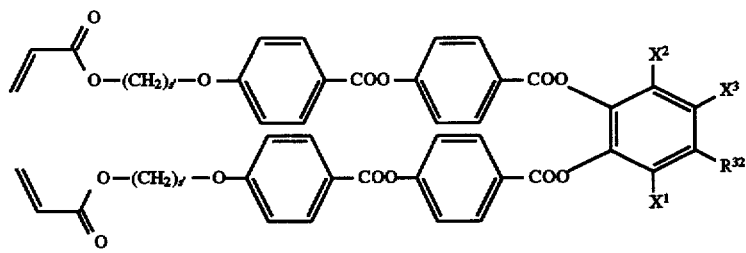

I-a

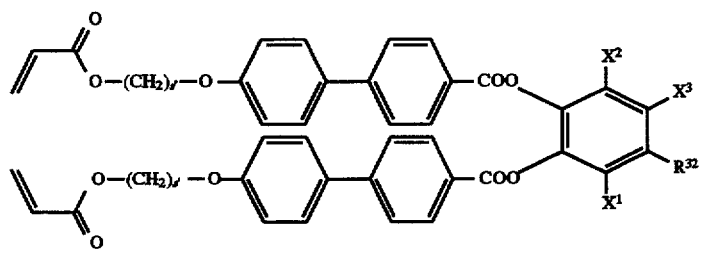

I-b

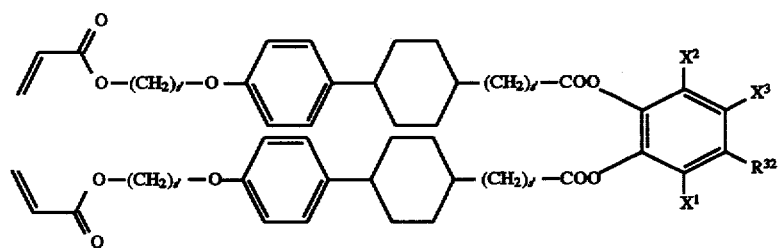

I-c wherein $R^{32}$ is fluorine, chlorine, cyano or alkoxycarbonyl; and $X^1$, $X^2$, $X^3$, and S' are as defined above.

Compounds of formula I-a in which $R^{32}$ is cyano or alkoxycarbonyl and each of $X^1$, $X^2$ and $X^3$ is hydrogen are particularly preferred.

Also preferred are compounds of formula I-B

$R^{33}$ is halogen, cyano or alkoxycarbonyl;

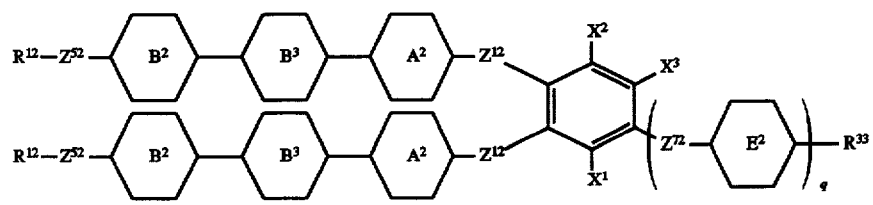

I-B q is 0 or 1; and each of $X^1, X^2$ and $X^3$ have the significance given above.

Particularly preferred are compounds of formula I-B in which q is 0, such as, for example, compounds of formulae Id–Ig

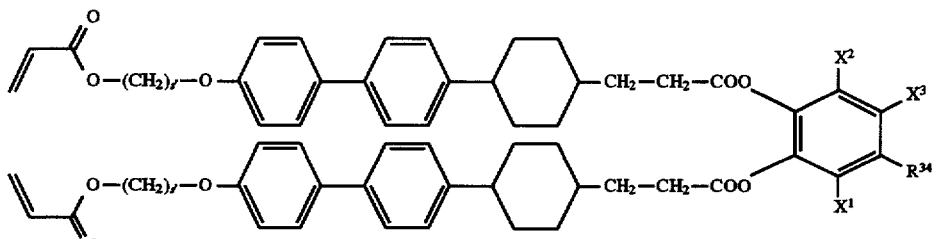

I-d

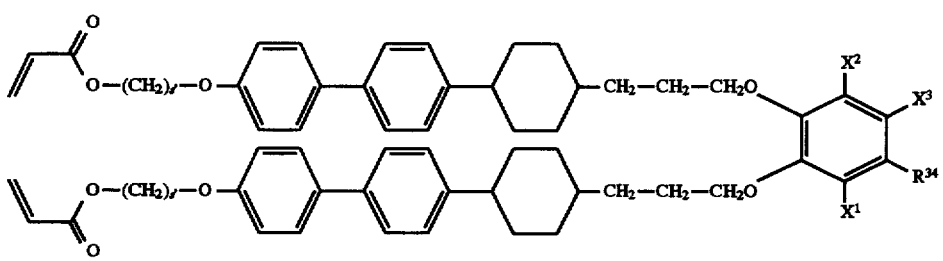

I-e

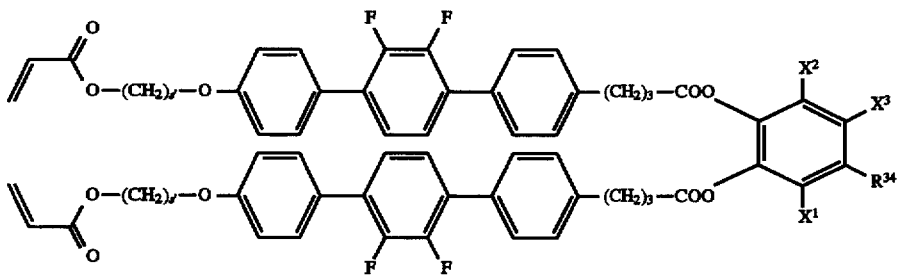

I-f

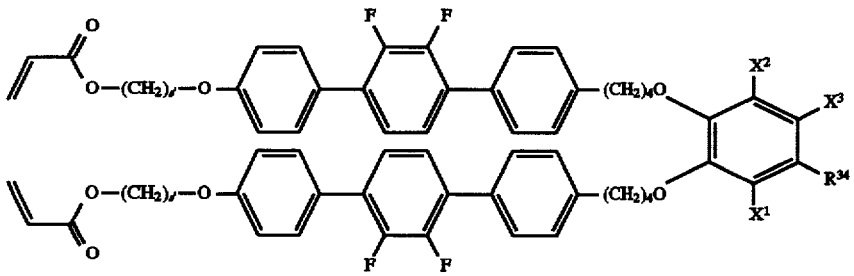

I-g wherein $R^{34}$ signifies fluorine, chlorine, cyano or alkoxycarbonyl; and $X^1$, $X^2$, $X^3$, and S' are as defined above.

The compounds of formulae I-A and I-B are very readily accessible synthetically and can be produced, for example, analogously to the methods illustrated in Schemes 1 to 10. Thus, 2-hydroxyphenols can be reacted with (ω-acryloyloxyalkyloxy)-substituted carboxylic acids in a manner known to those skilled in the art. This esterification can be effected, for example, via the corresponding methanesulphonic acid ester in tetrahydrofuran or in the presence of N,N'-dicyclohexylcarbodiimide (DCC) and 4-(dimethylamino)pyridine (DMAP) in dichloromethane or another suitable solvent such as e.g. chloroform. The 2-hydroxyphenols can also be reacted in a Mitsunobu reaction with (ω-acryloyloxyalkyloxy)-substituted benzyl alcohols. This etherification can be effected, for example, at room temperature in the presence of diethyl azodicarboxylate and triphenylphosphine in tetrahydrofuran or another suitable solvent such as e.g. N,N'-dimethylformamide. The 2-hydroxyphenols are known or can be prepared according to methods known to a person skilled in the art.

In the Schemes the symbols have the aforementioned significances.

Scheme 1
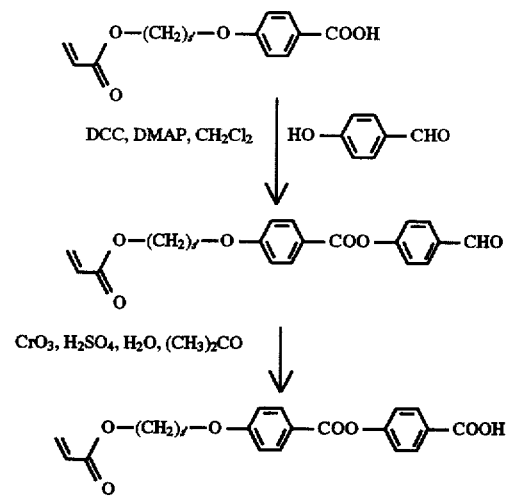
Scheme 2
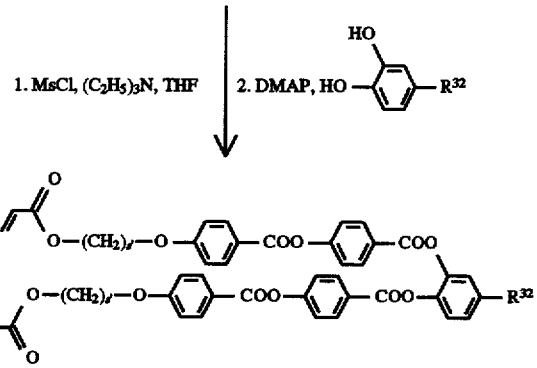
-continued
Scheme 2
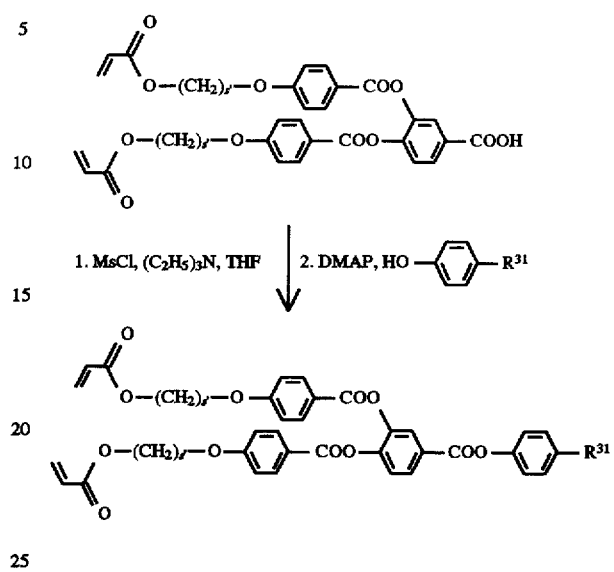
Scheme 3
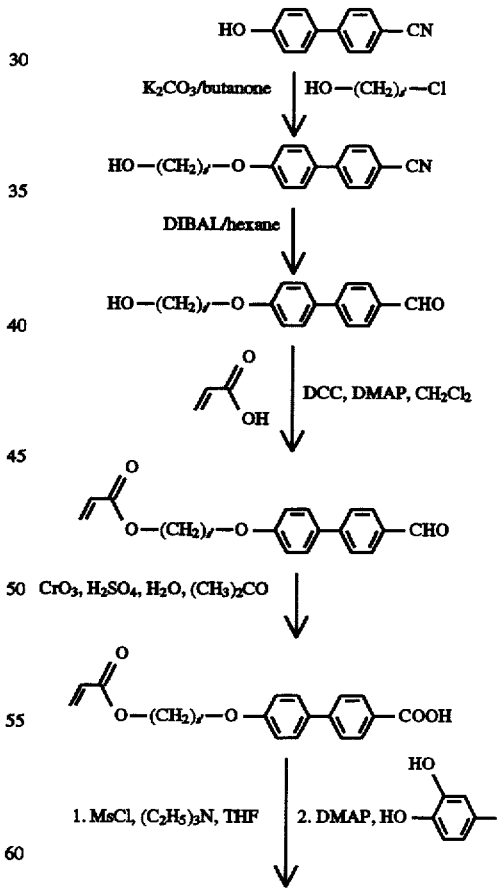

-continued
Scheme 3
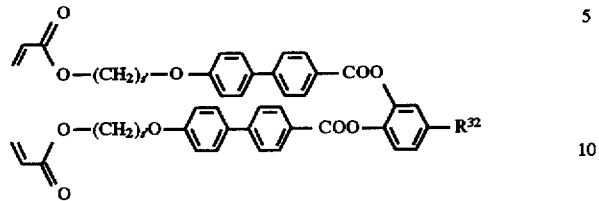
Scheme 4
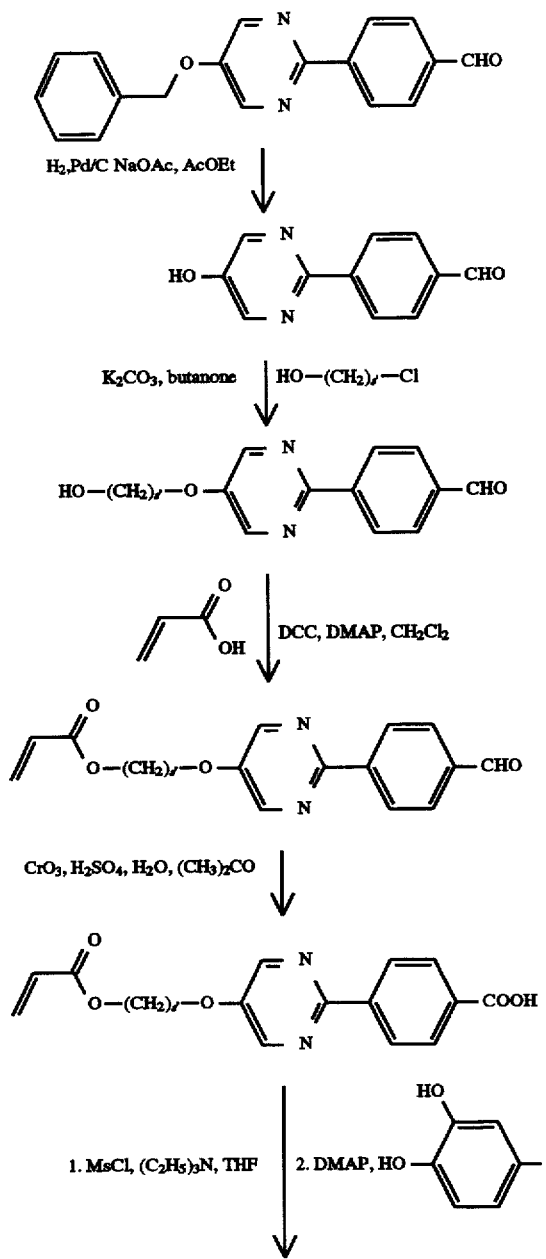

-continued
Scheme 4
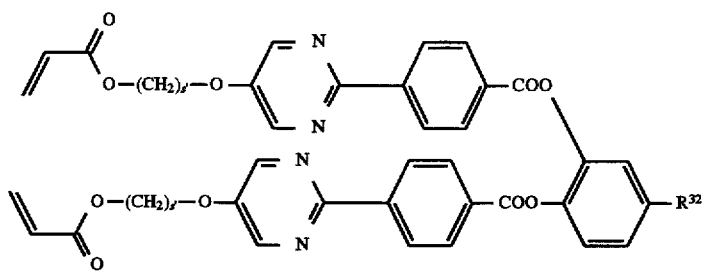
Scheme 5
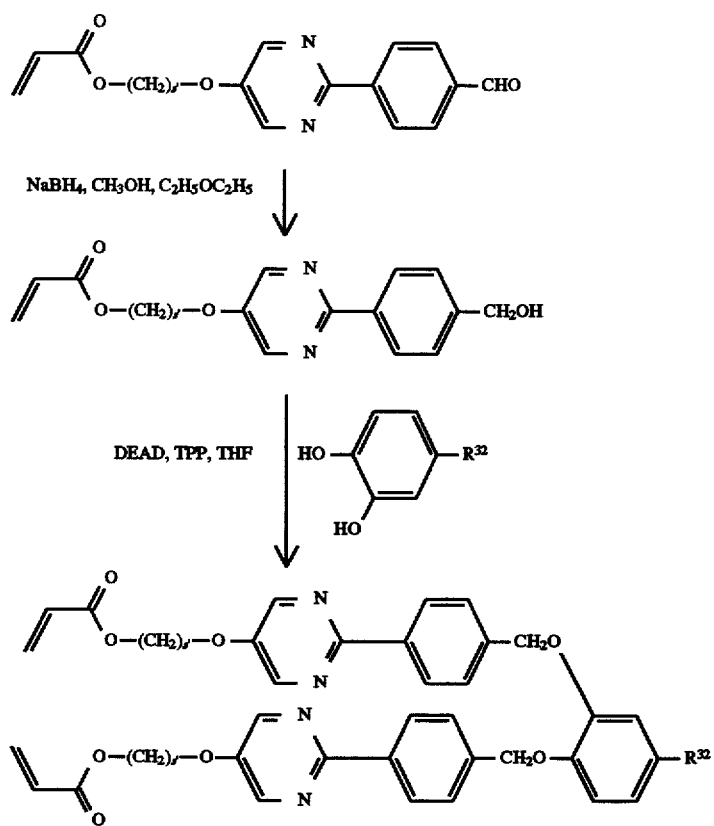
Scheme 6
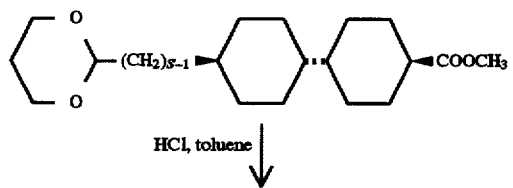
-continued
Scheme 6
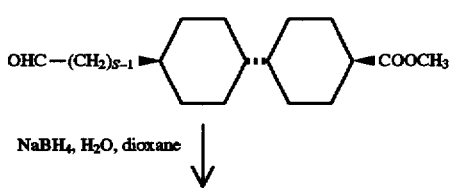

Scheme 6
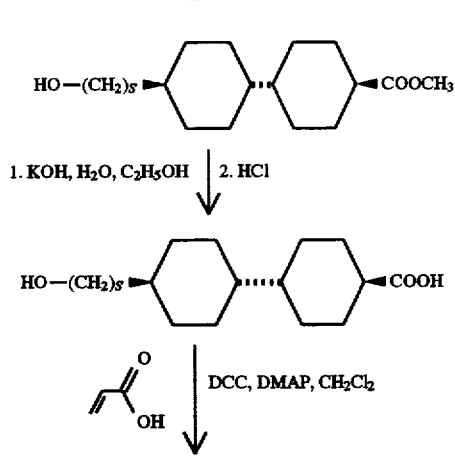
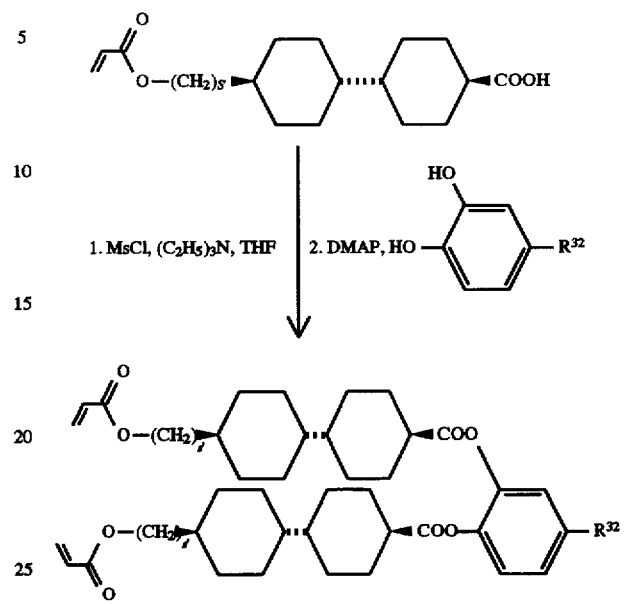
Scheme 7
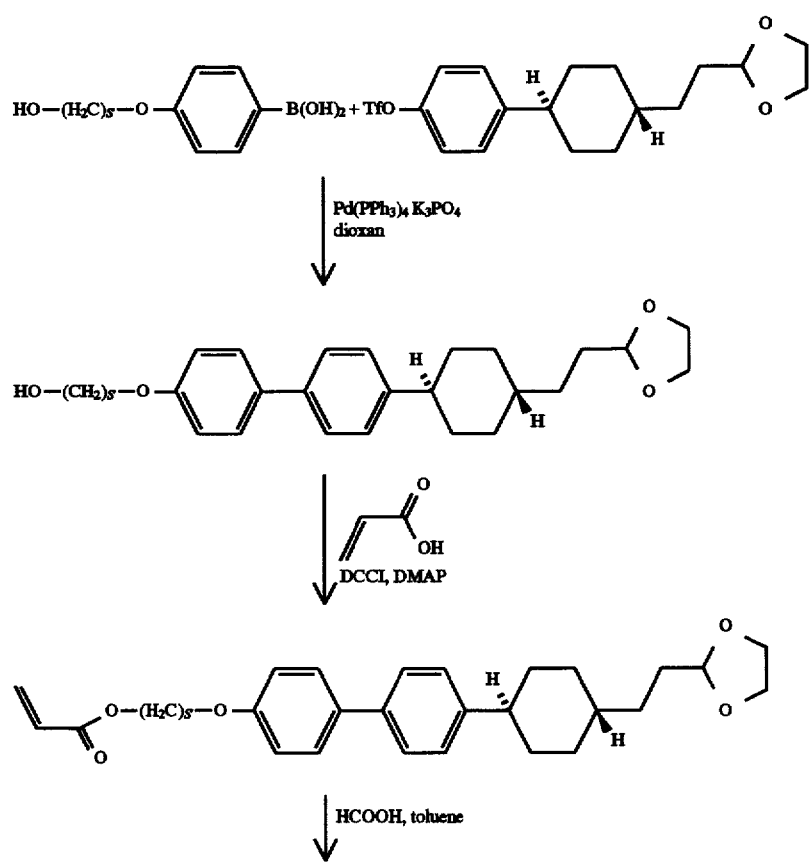

-continued
Scheme 7
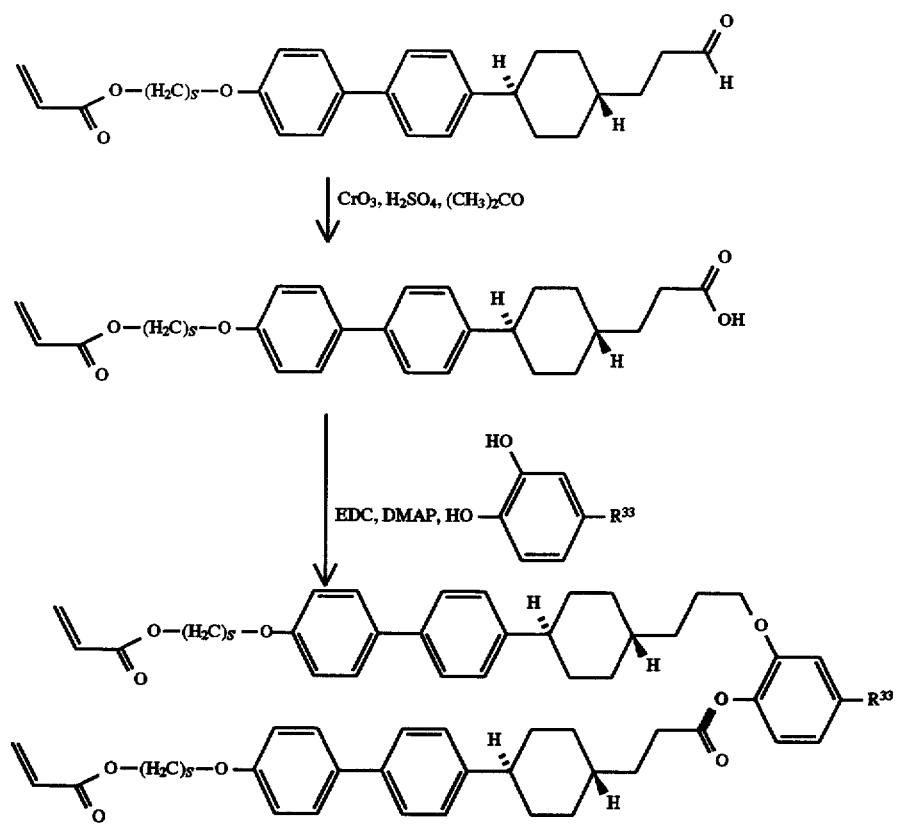
Scheme 8
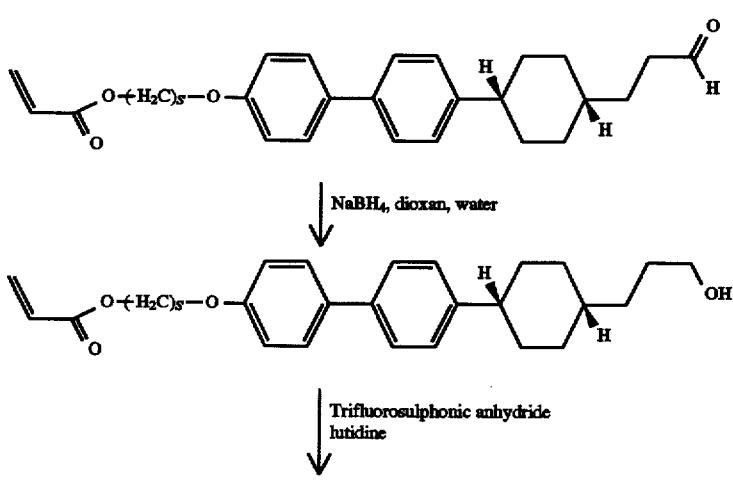

-continued
Scheme 8
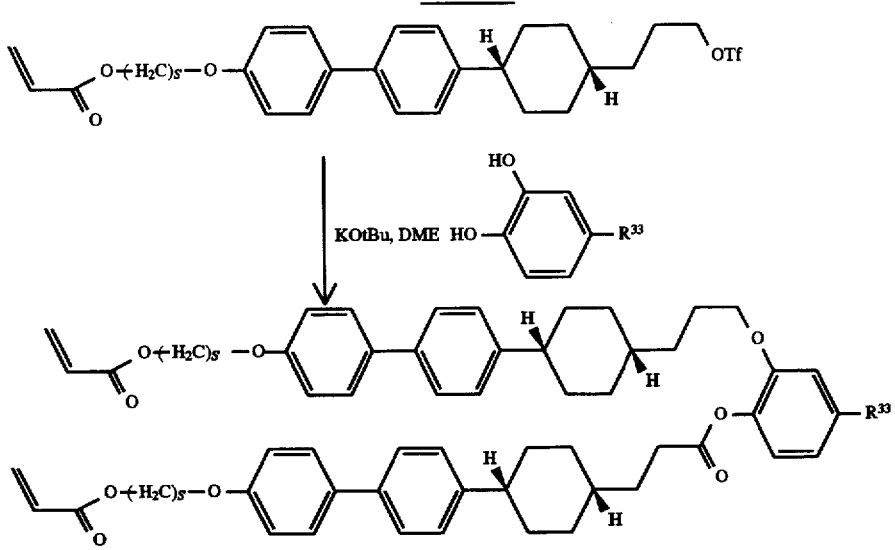
Scheme 9
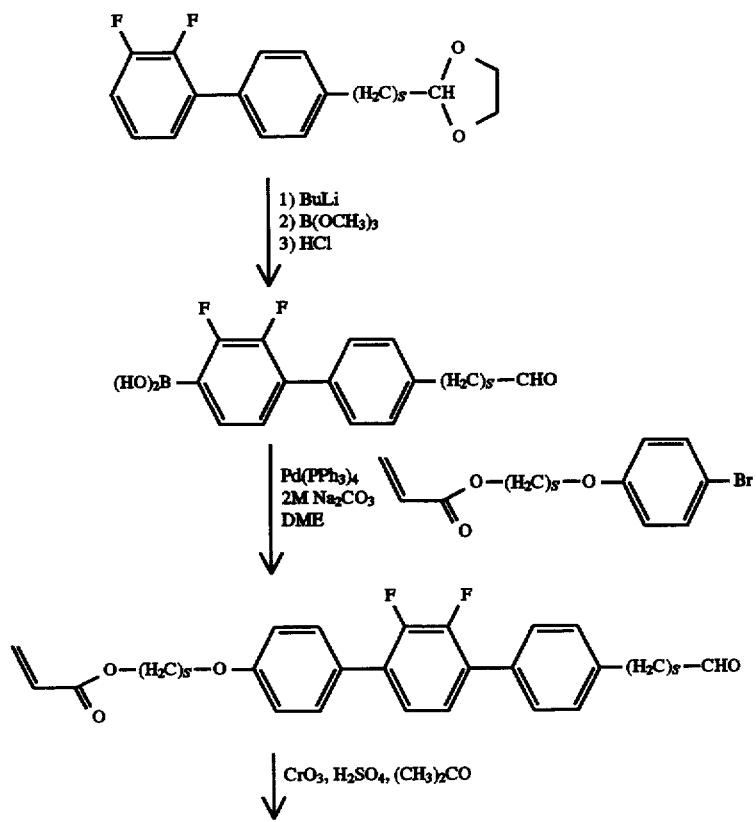

-continued
Scheme 9
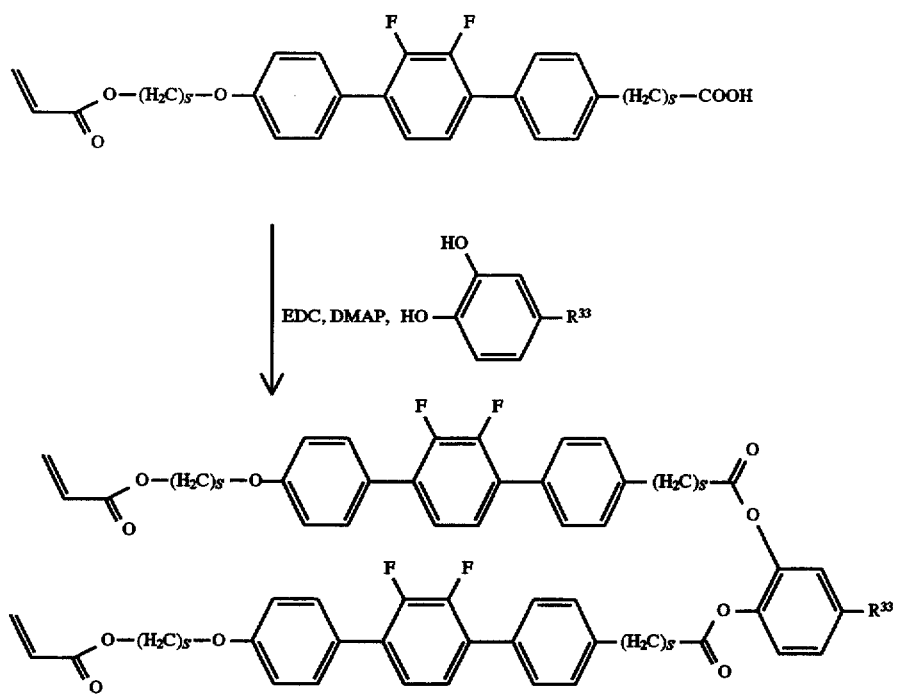
Scheme 10
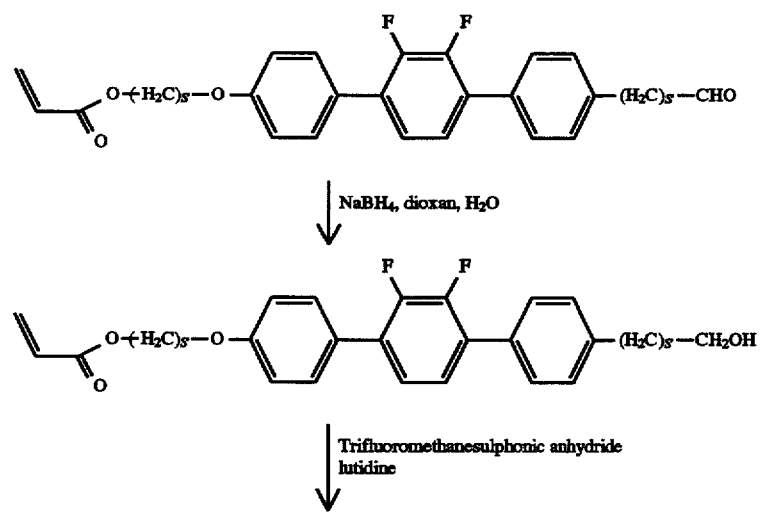

-continued
Scheme 10

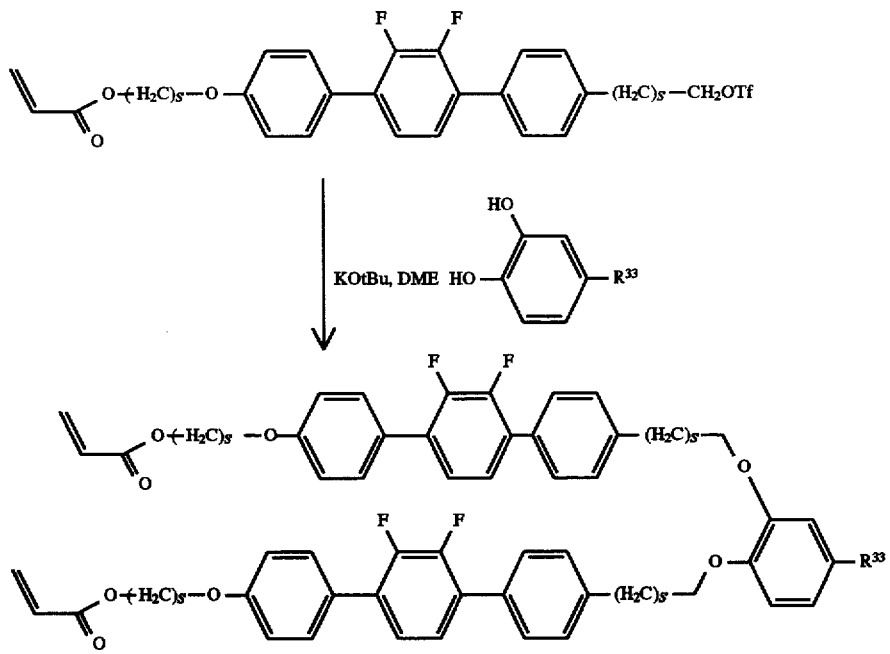

A small amount of BHT (2,6-di-tert.-butyl-4-methylphenol/"butylhydroxytoluene") is admixed in each stage in order to stop undesired thermal cross-linkage.

Compounds of formula I in which the cross-linkable side-chains are different can be produced by mono-esterifying 2-hydroxyphenols with an (ω-acryloyloxyalkyloxy)-substituted carboxylic acid. Subsequent esterification with a different (ω-acryloyloxyalkyloxy)-substituted carboxylic acid gives the asymmetric diester. The corresponding asymmetric diethers are accessible via a similar two-stage process. The starting materials are known and in part are commercially available.

The compounds of formula I can be used as single compounds or in the form of mixtures with one another and/or with other liquid crystal components.

The liquid crystalline mixtures in accordance with the invention contain at least 2 components, of which at least one component is a compound of formula I. A second component and optionally additional components can be further compounds of formula I or other known liquid crystalline compounds having a photo cross-linkable group. One or more chiral components can also be present in the mixture.

Having regard to the good solubility of the compounds of formula I and having regard to their good miscibility with one another, the content of compounds of formula I in the mixtures in accordance with the invention can be high and can amount to 100 wt. %.

The mixtures in accordance with the invention preferably contain, in addition to one or more compounds of formula I, one or more compounds from the group of compounds of the formulae

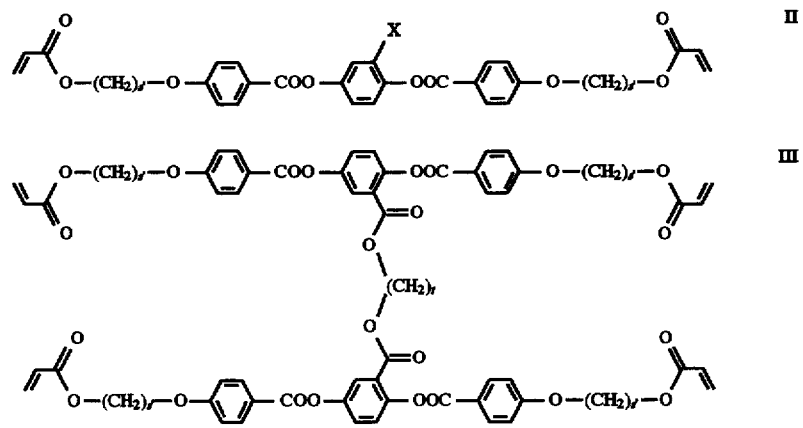

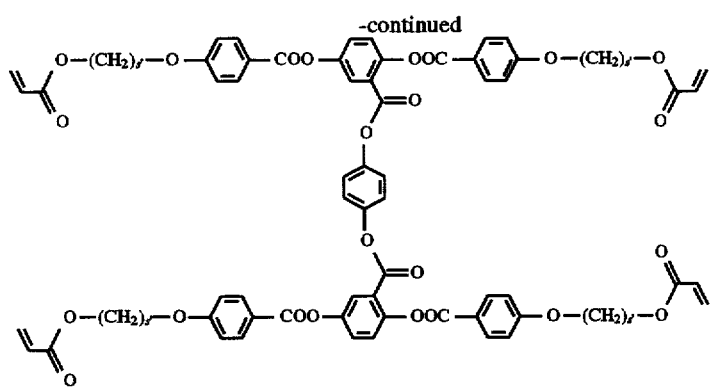
IV
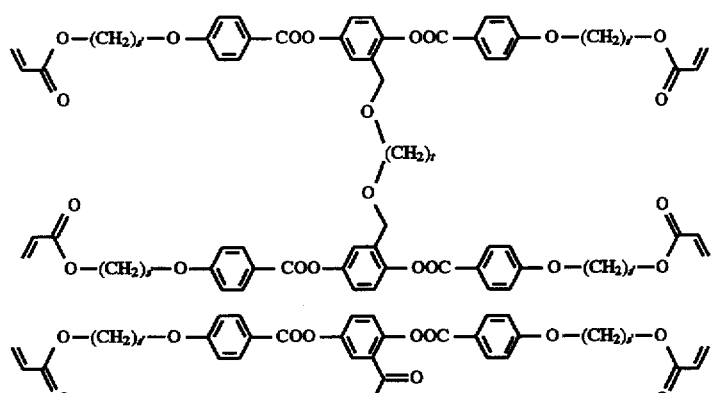
V
VI
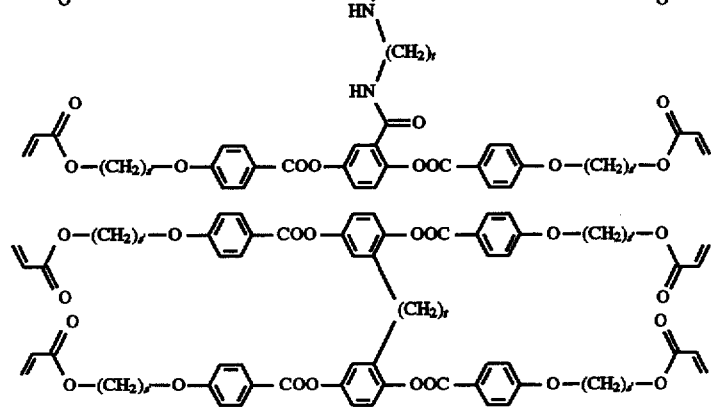
VII
VIII
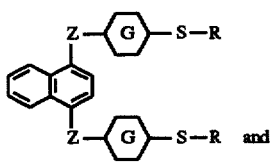
IX
wherein
X is hydrogen, fluorine, chlorine, bromine or methyl;
s' is a whole number of 3 to 12; and
t is a whole number of 2 to 12;
Z is —OCH$_2$— or —OOC—;
G is 1,4-phenylene or 2- or 3-fluoro-1,4-phenylene;
S is —(CH$_2$)$_{s'}$— or —(CH$_2$)$_{s'}$O—; and
R is CH$_2$=CH—COO—, CH$_2$=C(CH$_3$)—COO—, CH$_2$=CH—O— or
CH$_2$=CH—O— or $\underset{O}{H_2C-CH}$—.

The present invention provides a wide range of novel components and mixtures for the usual electro-optical fields of application of liquid crystals. The electro-optical devices can be constructed and used in manners well known to those of ordinary skill in the art.

The production of the compounds of formula I and of liquid crystalline mixtures containing these compounds is illustrated in more detail by the following Examples. C signifies a crystalline phase, S signifies a smectic phase, N signifies a nematic phase and I signifies the isotropic phase.

EXAMPLE 1

0.9g of triethylamine and then 0.5 g of methanesulphonyl chloride were added dropwise at −25° C. while stirring to a solution of 2.0 g of 4-(4-[8-acryloyloxyoctyloxy]phenylcarbonyloxy)benzoic acid in 40 ml of tetrahydrofuran. The reaction mixture was stirred at −25° C. for 1 hour, treated with 0.28 g of 3,4-dihydroxybenzonitrile and 0.05 g of 4-(dimethylamino)pyridine, stirred at room temperature overnight, poured into 100 ml of water and then extracted three times with 50 ml of diethyl ether each time. The organic phases were combined, washed twice with 100 ml of water each time, dried over magnesium sulphate, filtered and the filtrate was concentrated. Chromatographic purification of the residue on silica gel with cyclohexane/ethyl acetate (vol. 8:2) and two-fold recrystallization from a cyclohexane/ethyl acetate mixture (vol. 8:2) of the fractions which were pure according to thin-layer chromatography gave 1.2 g of 3,4-bis[4-(4-[8-acryloyloxyoctyloxy]phenylcarbonyloxy)phenylcarbonyloxy]benzonitrile; m.p. (C-S$_A$) 70° C., S$_A$-N 139° C., cl.p. (N-I) 152° C.

The 4-(4-[8-acryloyloxyoctyloxy]phenylcarbonyloxy)benzoic acid used as the starting material was prepared as follows:

(a). 3.9 g of N,N'-dicyclohexylcarbodiimide were added at 0° C. within 15 minutes while stirring to a solution of 1.9 g of 4-hydroxybenzaldehyde, 5.0 g of 4-[8-acryloyloxyoctyloxy]benzoic acid and 0.1 g of 4-(dimethylamino)pyridine in 100 ml of dichloromethane. The reaction mixture was stirred at room temperature overnight, filtered and the filtrate was concentrated. Chromatographic purification of the residue on silica gel with cyclohexane/ethyl acetate (vol. 8:2) and two-fold recrystallization from ethyl acetate of the fractions which were pure according to thin-layer chromatography gave 5.5 g of 4-(4-[8-acryloyloxyoctyloxy]phenylcarbonyloxy)benzaldehyde; m.p. 73° C.

(b). A solution of 5.5 g of 4-(4-[8-acryloyloxyoctyloxy]phenylcarbonyloxy)benzaldehyde in 100 ml of acetone was treated dropwise with 25 ml of Jones' reagent. The mixture was stirred at room temperature overnight, poured into 100 ml of water and extracted three times with 50 ml of ethyl acetate each time. The organic phases were combined, washed twice with 100 ml of water each time, dried over magnesium sulphate, filtered and the filtrate was concentrated. The residue was recrystallized from ethyl acetate. This gave 3.5 g of 4-(4-[8-acryloyloxyoctyloxy]phenylcarbonyloxy)benzoic acid; m.p. (C-N) 116° C., cl.p. (N-I) 240° C. (decomposition).

The following compounds can be prepared in an analogous manner:

3,4-bis[4-(4-[3-Acryloyloxypropyloxy]phenylcarbonyloxy)phenylcarbonyloxy]benzonitrile;

3,4-bis[4-(4-[4-acryloyloxybutyloxy]phenylcarbonyloxy)phenylcarbonyloxy]benzonitrile;

3,4-bis[4-(4-[5-acryloyloxypentyloxy]phenylcarbonyloxy)phenylcarbonyloxy]benzonitrile;

3,4-bis[4-(4-[6-acryloyloxyhexyloxy]phenylcarbonyloxy)phenylcarbonyloxy]benzonitrile;

3,4-bis[4-(4-[7-acryloyloxyheptyloxy]phenylcarbonyloxy)phenylcarbonyloxy]benzonitrile;

3,4-bis[4-(4-[9-acryloyloxynonyloxy]phenylcarbonyloxy)phenylcarbonyloxy]benzonitrile;

3,4-bis[4-(4-[10-acryloyloxydecyloxy]phenylcarbonyloxy)phenylcarbonyloxy]benzonitrile;

3,4-bis[4-(4-[11-acryloyloxyundecyloxy]phenylcarbonyloxy)phenylcarbonyloxy]benzonitrile;

3,4-bis[4-(4-[12-acryloyloxydodecyloxy]phenylcarbonyloxy)phenylcarbonyloxy]benzonitrile;

1,2-bis[4-(4-[8-acryloyloxyoctyloxy]phenylcarbonyloxy)phenylcarbonyloxy]benzene; m.p. (C-S$_A$) 89° C., S$_A$-N, 105° C., cl.p. (N-I) 107° C.;

methyl 3,4-bis[4-(4-[8-acryloyloxyoctyloxy]phenylcarbonyloxy)phenylcarbonyloxy]benzoate;

ethyl 3,4-bis[4-(4-[8-acryloyloxyoctyloxy]phenylcarbonyloxy)phenylcarbonyloxy]benzoate; m.p. (C-S$_A$) 25° C., cl.p. (S$_A$-I) 150° C.;

3,4-bis[4-(4-[8-acryloyloxyoctyloxy]phenylcarbonyloxy)phenylcarbonyloxy]toluene;

3,4-bis[4-(4-[8-acryloyloxyoctyloxy]phenylcarbonyloxy)phenylcarbonyloxy]-1-ethylbenzene;

3,4-bis[4-(4-[8-acryloyloxyoctyloxy]phenylcarbonyloxy)phenylcarbonyloxy]-1-propylbenzene.

EXAMPLE 2

0.9g of triethylamine and then 0.5 g of methanesulphonyl chloride were added dropwise at −25° C. while stirring to a solution of 0.4 g of 3,4-bis(4-[8-acryloyloxyoctyloxy]phenylcarbonyloxy)benzoic acid in 40 ml of tetrahydrofuran. The reaction mixture was stirred at −25° C. for 1 hour, then treated with 0.06 g of 2-fluoro-4-hydroxybenzonitrile and 0.05 g of 4-(dimethylamino)pyridine in 40 ml of tetrahydrofuran, stirred at room temperature overnight, poured into 100 ml of water and then extracted three times with 50 ml of diethyl ether each time. The organic phases were combined, washed twice with 100 ml of water each time, dried over magnesium sulphate, filtered and the filtrate was concentrated. Chromatographic purification of the residue on silica gel with cyclohexane/ethyl acetate (vol. 8:2) and two-fold recrystallization from ethyl alcohol of the fractions which were pure according to thin-layer chromatography gave 1.2 g of 3,4-bis[4-(4-[8-acryloyloxyoctyloxy]phenylcarbonyloxy)phenylcarbonyloxy]-2-fluorobenzonitrile; m.p. (C-I) 85° C., cl.p. (N-I) 3° C.

The 3,4-bis(4-[8-acryloyloxyoctyloxy]phenylcarbonyloxy)benzoic acid used as the starting material was prepared as follows:

(a). 0.6 g of triethylamine and then 0.4 g of methanesulphonyl chloride were added dropwise at −25° C. while stirring to a solution of 1.0 g of 4-(8-acryloyloxyoctyloxy)benzoic acid in 40 ml of tetrahydrofuran. The reaction mixture was stirred at −25° C. for 1 hour, then treated with 0.20 g of 4-hydroxybenzaldehyde and 0.03 g of 4-(dimethylamino)pyridine in 40 ml of tetrahydrofuran, stirred at room temperature overnight, poured into 100 ml of water and then extracted three times with 50 ml of diethyl ether each time. The organic phases were combined, washed twice with 100 ml of water each time, dried over magnesium sulphate, filtered and the filtrate was concentrated. Chromatographic purification of the residue on silica gel with cyclohexane/ethyl acetate (vol. 8:2) and two-fold recrystallization from a cyclohexane/ethyl acetate mixture (vol. 8:2) of the fractions which were pure according to thin-layer chromatography gave 0.6 g of 3,4-bis (4-[8-acryloyloxyoctyloxy]phenylcarbonyloxy) benzaldehyd; m.p. (C-I) 56° C.

(b). A solution of 0.6 g of 3,4-bis(4-[8-acryloyloxyoctyloxy]phenylcarbonyloxy) benzaldehyde in 20 ml of acetone was treated dropwise at 0° C. with 2 ml of Jones' reagent. The mixture was stirred at 0° C. for 1 hour and then at room temperature overnight, poured into 100 ml of water and filtered, the filter material was washed with water and then dried. This gave 0.4 g of 3,4-bis(4-[8-acryloyloxyoctyloxy] phenylcarbonyloxy)benzoic acid.

The following compounds can be prepared in an analogous manner:

3,4-bis[4-(4-[3-Acryloyloxypropyloxy] phenylcarbonyloxy)phenylcarbonyloxy]-2-fluorobenzonitrile;

3,4-bis[4-(4-[4-acryloyloxybutyloxy]phenylcarbonyloxy) phenylcarbonyloxy]-2-fluorobenzonitrile;

3,4-bis[4-(4-[5-acryloyloxypentyloxy] phenylcarbonyloxy)phenylcarbonyloxy]-2-fluorobenzonitrile;

3,4-bis[4-(4-[6-acryloyloxyhexyloxy] phenylcarbonyloxy)phenylcarbonyloxy]-2-fluorobenzonitrile;

3,4-bis[4-(4-[7-acryloyloxyheptyloxy] phenylcarbonyloxy)phenylcarbonyloxy]-2-fluorobenzonitrile;

GG3,4-bis[4-(4-[9-acryloyloxynonyloxy] phenylcarbonyloxy)phenylcarbonyloxy]-2-fluorobenzonitrile;

3,4-bis[4-(4-[10-acryloyloxydecyloxy] phenylcarbonyloxy)phenylcarbonyloxy]-2-fluorobenzonitrile;

3,4-bis[4-(4-[11-acryloyloxyundecyloxy] phenylcarbonyloxy)phenylcarbonyloxy]-2-fluorobenzonitrile;

3,4-bis[4-(4-[12-acryloyloxydodecyloxy] phenylcarbonyloxy)phenylcarbonyloxy]-2-fluorobenzonitrile;

3,4-bis[4-(4-[6-acryloyloxyhexyloxy] phenylcarbonyloxy)phenylcarbonyloxy]-1-fluorobenzene;

3,4-bis[4-(4-[6-acryloyloxyhexyloxy] phenylcarbonyloxy)phenylcarbonyloxy]-1-chlorobenzene;

3,4-bis[4-(4-[6-acryloyloxyhexyloxy] phenylcarbonyloxy)phenylcarbonyloxy]-1-bromobenzene;

3,4-bis[4-(4-[6-acryloyloxyhexyloxy] phenylcarbonyloxy)phenylcarbonyloxy]-1,2-difluorobenzene;

3,4-bis[4-(4-[6-acryloyloxyhexyloxy] phenylcarbonyloxy)phenylcarbonyloxy]-1,2-dichloroobenzene;

3,4-bis[4-(4-[6-acryloyloxyhexyloxy] phenylcarbonyloxy)phenylcarbonyloxy]-1,2-dicyanobenzene;

3,4-bis[4-(4-[6-acryloyloxyhexyloxy] phenylcarbonyloxy)phenylcarbonyloxy]-1-chloro-2-fluorobenzene.

EXAMPLE 3

0.9 g of triethylamine and then 0.5 g of methanesulphonyl chloride were added dropwise at −25° C. while stirring to a solution of 2.0 g of 4-(8-acryloyloxyoctyloxy)biphenyl-4'-carboxylic acid in 40 ml of tetrahydrofuran. The reaction mixture was stirred at −25° C. for 1 hour, then treated with 0.25 g of 3,4-dihydroxybenzonitrile and 0.05 g of 4-(dimethylamino)pyridine, stirred at room temperature overnight, poured into 100 ml of water and then extracted three times with 50 ml of diethyl ether each time. The organic phases were combined, washed twice with 100 ml of water each time, dried over magnesium sulphate, filtered and the filtrate was concentrated. Chromatographic purification of the residue on silica gel with cyclohexane/ethyl acetate (vol. 8:2) and two-fold recrystallization from a cyclohexane/ ethyl acetate mixture (vol. 8:2) of the fractions which were pure according to thin-layer chromatography gave 1.0 g of 3,4-bis[4-(8-acryloyloxyoctyloxy)biphenyl-4'-carbonyloxy] benzonitrile.

The 4-(8-acryloyloxyoctyloxy)biphenyl-4'-carboxylic acid used as the starting material was prepared as follows:

(a). A solution of 5.0 g of 4'-hydroxybiphenyl-4-carbonitrile and 5.1 g of 8-chloro-1-octanol in 100 ml of ethyl methyl ketone was treated with 14.1 g of finely powdered potassium carbonate and the mixture was heated under slight reflux overnight. The suspension was suction filtered and the filtrate was concentrated in a vacuum. Chromatography of the residue on silica gel with hexane/ethyl acetate (vol. 1:1) gave 4.9 g of 4'-(8-hydroxyoctyloxy)biphenyl-4-carbonitrile.

(b). A solution of 4.9 g of 4-cyano-4'-(8-hydroxyoctyloxy) biphenyl in 25 ml of toluene was treated at 20° C. with 50 ml of a 1.2M solution of diisobutylaluminium hydride in toluene and the mixture was stirred at room temperature overnight. The reaction mixture was poured into 100 ml of 1.0N sulphuric acid and extracted twice with 50 ml of ethyl acetate each time. The organic phases were washed with 50 ml of water, dried over magnesium sulphate and concentrated. Chromatography of the residue on silica gel with hexane/ethyl acetate (vol. 8:2) and recrystallization from ethyl alcohol of the fractions which were pure according to thin-layer chromatography gave 3.8 g of 4-formyl-4'-(8-hydroxyoxyoctyloxy)biphenyl.

(c). 2.9 g of N,N'-dicyclohexylcarbodiimide were added within 5 minutes while stirring to a solution of 3.8 g of 4-formyl-4'-(8-hydroxyoctyloxy)biphenyl, 0.9 g of acrylic acid and 0.05 g of 4-(dimethylamino)pyridine in 25 ml of dichloromethane. The reaction mixture was stirred overnight, filtered and then concentrated. Chromatography of the residue on silica gel with hexane/ ethyl acetate (vol. 8:2) and recrystallization from ethyl alcohol of the fractions which were pure according to thin-layer chromatography gave 2.5 g of 4-formyl-4'-(8-acryloyloxyoctyloxy)biphenyl.

(d). A solution of 2.5 g of 4-formyl-4'-(8-acryloyloxyoctyloxy)biphenyl in 100 ml of acetone was treated dropwise with 10 ml of Jones' reagent. The mixture was stirred at room temperature for 1 hour and then at room temperature overnight, poured into 100 ml of water and then extracted three times with 50 ml of ethyl acetate each time. The combined organic phases were washed twice with 100 ml of water each time, dried over magnesium sulphate, filtered and the filtrate was concentrated. The residue was recrystallized from ethyl acetate. This gave 1.6 g of 4-(8-acryloyloxyoctyloxy)biphenyl-4'-carboxylic acid.

The following compounds can be prepared in an analogous manner:

3,4-bis[4-(3-Acryloyloxypropyloxy)biphenyl-4'-carbonyloxy]benzonitrile;

3,4-bis[4-(4-acryloyloxybutyloxy)biphenyl-4'-carbonyloxy]benzonitrile;

3,4-bis[4-(5-acryloyloxypentyloxy)biphenyl-4'-carbonyloxy]benzonitrile;

3,4-bis[4-(6-acryloyloxyhexyloxy)biphenyl-4'-carbonyloxy]benzonitrile;

3,4-bis[4-(7-acryloyloxyheptyloxy)biphenyl-4'-carbonyloxy]benzonitrile;

3,4-bis[4-(9-acryloyloxynonyloxy)biphenyl-4'-carbonyloxy]benzonitrile;

3,4-bis[4-(10-acryloyloxydecyloxy)biphenyl-4'-carbonyloxy]benzonitrile;

3,4-bis[4-(11-acryloyloxyundecyloxy)biphenyl-4'-carbonyloxy]benzonitrile;

3,4-bis[4-(12-acryloyloxydodecyloxy)biphenyl-4'-carbonyloxy]benzonitrile;

methyl 3,4-bis[4-(8-acryloyloxyoctyloxy)biphenyl-4'-carbonyloxy]benzoate;

ethyl 3,4-bis[4-(8-acryloyloxyoctyloxy)biphenyl-4'-carbonyloxy]benzoate;

propyl 3,4-bis[4-(8-acryloyloxyoctyloxy)biphenyl-4'-carbonyloxy]benzoate;

3,4-bis[4-(8-acryloyloxyoctyloxy)biphenyl-4'-carbonyloxy]toluene;

3,4-bis[4-(8-acryloyloxyoctyloxy)biphenyl-4'-carbonyloxy]-1-ethylbenzene;

3,4-bis[4-(8-acryloyloxyoctyloxy)biphenyl-4'-carbonyloxy]-1-propylbenzene;

EXAMPLE 4

0.9 g of triethylamine and then 0.5 g of methanesulphonyl chloride were added dropwise at −25° C. while stirring to a solution of 2.0 g of 4-(5-[8-acryloyloxyoctyloxy]pyrimidin-2-yl)benzoic acid in 40 ml of tetrahydrofuran. The reaction mixture was stirred at −25° C. for 1 hour, then treated with 0.28 g of 3,4-dihydroxybenzonitrile and 0.05 g of 4-(dimethylamino)pyridine, stirred at room temperature overnight, poured into 100 ml of water and then extracted three times with 50 ml of diethyl ether each time. The organic phases were combined, washed twice with 100 ml of water each time, dried over magnesium sulphate, filtered and the filtrate was concentrated. Chromatographic purification of the residue on silica gel with cyclohexane/ethyl acetate (vol. 8:2) and two-fold recrystallization from a cyclohexane/ethyl acetate mixture (vol. 8:2) of the fractions which were pure according to thin-layer chromatography gave 1.1 g of 3,4-bis[4-(5-[8-acryloyloxyoctyloxy]pyrimidin-2-yl)phenylcarbonyloxy]benzonitrile.

The 4-(5-[8-acryloyloxyoctyloxy]pyrimidin-2-yl)benzoic acid used as the starting material was prepared as follows:

(a). A mixture of 10.0 g of 4-(5-benzyloxypyrimidin-2-yl)benzaldehyde, 0.2 g of sodium carbonate and 250 ml of ethyl acetate was treated with 1.0 g of palladium on active charcoal (10%) and hydrogenated at normal pressure and room temperature until the hydrogen uptake came to a standstill. The inorganic material was filtered off over Sillit and the filtrate was concentrated. Recrystallization of the crude product from hexane gave 6.1 g of pure 4-(5-hydroxypyrimidin-2-yl)benzaldehyde.

(b). A solution of 6.1 g of 4-(5-hydroxypyrimidin-2-yl)benzaldehyde and 6.0 g of 8-chloro-1-octanol in 100 ml of ethyl methyl ketone was treated with 16.9 g of finely powdered potassium carbonate and the mixture was heated under slight reflux overnight. The suspension was suction filtered and the filtrate was concentrated in a vacuum. Chromatography of the residue on silica gel with hexane/ethyl acetate (vol. 1:1) gave 5.5 g of 4-(5-[8-hydroxyoctyloxy]-pyrimidin-2-yl)benzaldehyde.

(c). 4.2 g of N,N'-dicyclohexylcarbodiimide were added within 5 minutes while stirring to a solution of 5.5 g of 4-(5-[8-hydroxyoctyloxy]pyrimidin-2-yl)benzaldehyde, 1.2 g of acrylic acid and 0.2 g of 4-(dimethylamino)pyridine in 25 ml of dichloromethane. The reaction mixture was stirred overnight, filtered and the filtrate was concentrated. Chromatography of the residue on silica gel with hexane/ethyl acetate (vol. 8:2) and recrystallization from ethyl alcohol of the fractions which were pure according to thin-layer chromatography gave 4.8 g of 4-(5-[8-acryloyloxyoctyloxy]pyrimidin-2-yl)benzaldehyde.

(d). A solution of 3.2 g of 4-(5-[8-acryloyloxyoctyloxy]pyrimidin-2-yl)benzaldehyde in 100 ml of acetone was treated dropwise with 20 ml of Jones' reagent. The mixture was stirred at room temperature overnight, poured into 100 ml of water and then extracted three times with 50 ml of ethyl acetate each time. The organic phases were combined, washed twice with 100 ml of water each time, dried over magnesium sulphate, filtered and the filtrate was concentrated. The residue was recrystallized from ethyl acetate. This gave 2.0 g of 4-(5-[8-acryloyloxyoctyloxy]pyrimidin-2-yl)benzoic acid.

The following compounds can be prepared in an analogous manner:

3,4-bis[4-(5-[3-acryloyloxypropyloxy]pyrimidin-2-yl)phenylcarbonyloxy]benzonitrile;

3,4-bis[4-(5-[4-acryloyloxybutyloxy]pyrimidin-2-yl)phenylcarbonyloxy]benzonitrile;

3,4-bis[4-(5-[5-acryloyloxypentyloxy]pyrimidin-2-yl)phenylcarbonyloxy]benzonitrile;

3,4-bis[4-(5-[6-acryloyloxyhexyloxy]pyrimidin-2-yl)phenylcarbonyloxy]benzonitrile;

3,4-bis[4-(5-[7-acryloyloxyheptyloxy]pyrimidin-2-yl)phenylcarbonyloxy]benzonitrile;

3,4-bis[4-(5-[9-acryloyloxynonyloxy]pyrimidin-2-yl)phenylcarbonyloxy]benzonitrile;

3,4-bis[4-(5-[10-acryloyloxydecyloxy]pyrimidin-2-yl)phenylcarbonyloxy]benzonitrile;

3,4-bis[4-(5-[11-acryloyloxyundecyloxy]pyrimidin-2-yl)phenylcarbonyloxy]benzonitrile;

3,4-bis[4-(5-[12-acryloyloxydodecyloxy]pyrimidin-2-yl)phenylcarbonyloxy]benzonitrile;

methyl 3,4-bis[4-(5-[8-acryloyloxyoctyloxy]pyrimidin-2-yl)phenylcarbonyloxy]benzoate;

ethyl 3,4-bis[4-(5-[8-acryloyloxyoctyloxy]pyrimidin-2-yl)phenylcarbonyloxy]benzoate;

propyl 3,4-bis[4-(5-[8-acryloyloxyoctyloxy]pyrimidin-2-yl)phenylcarbonyloxy]benzoate;

3,4-bis[4-(5-[12-acryloyloxydodecyloxy]pyrimidin-2-yl)phenylcarbonyloxy]toluene;

3,4-bis[4-(5-[12-acryloyloxydodecyloxy]pyrimidin-2-yl)phenylcarbonyloxy]-1-ethylbenzene;

3,4-bis[4-(5-[12-acryloyloxydodecyloxy]pyrimidin-2-yl)phenylcarbonyloxy]-1-propylbenzene;

3,4-bis[2-(4-[3-acryloyloxypropyloxy]phenyl)pyridin-5-ylcarbonyloxy]benzonitrile;

3,4-bis[2-(4-[4-acryloyloxybutyloxy]phenyl)pyridin-5-ylcarbonyloxy]benzonitrile;

3,4-bis[2-(4-[5-acryloyloxypentyloxy]phenyl)pyridin-5-ylcarbonyloxy]benzonitrile;

3,4-bis[2-(4-[6-acryloyloxyhexyloxy]phenyl)pyridin-5-ylcarbonyloxy]benzonitrile;

3,4-bis[2-(4-[7-acryloyloxyheptyloxy]phenyl)pyridin-5-ylcarbonyloxy]benzonitrile;

3,4-bis[2-(4-[8-acryloyloxyoctyloxy]phenyl)pyridin-5-ylcarbonyloxy]benzonitrile;

3,4-bis[2-(4-[9-acryloyloxynonyloxy]phenyl)pyridin-5-ylcarbonyloxy]benzonitrile;

3,4-bis[2-(4-[10-acryloyloxydecyloxy]phenyl)pyridin-5-ylcarbonyloxy]benzonitrile;

3,4-bis[2-(4-[11-acryloyloxyundecyloxy]phenyl)pyridin-5-ylcarbonyloxy]benzonitrile;

3,4-bis[2-(4-[12-acryloyloxydodecyloxy]phenyl)pyridin-5-ylcarbonyloxy]benzonitrile;

methyl 3,4-bis[2-(4-[3-acryloyloxypropyloxy]phenyl)pyridin-5-ylcarbonyloxy]benzoate;

ethyl 3,4-bis[2-(4-[3-acryloyloxypropyloxy]phenyl)pyridin-5-ylcarbonyloxy]benzoate;

propyl 3,4-bis[2-(4-[3-acryloyloxypropyloxy]phenyl)pyridin-5-ylcarbonyloxy]benzoate;

3,4-bis[2-(4-[3-acryloyloxypropyloxy]phenyl)pyridin-5-ylcarbonyloxy]toluene;

3,4-bis[2-(4-[3-acryloyloxypropyloxy]phenyl)pyridin-5-ylcarbonyloxy]-1-ethylbenzene;

3,4-bis[2-(4-[3-acryloyloxypropyloxy]phenyl)pyridin-5-ylcarbonyloxy]-1-propylbenzene.

EXAMPLE 5

A solution of 1.1 g of 4-(5-[8-acryloyloxyoctyloxy]pyrimidin-2-yl)benzyl alcohol, 0.2 g of 3,4-dihydroxybenzonitrile, 0.5 g of diethyl azodicarboxylate, 0.7 g of triphenylphosphine and 50 ml of tetrahydrofuran was stirred overnight and then concentrated. The residue was suspended in 50 ml of hot hexane and filtered. The filtrate was concentrated. Chromatographic purification of the residue on silica gel with cyclohexane/ethyl acetate (vol. 8:2) and two-fold recrystallization from a cyclohexane/ethyl acetate mixture (vol. 8:2) of the fractions which were pure according to thin-layer chromatography gave 1.2 g of 3,4-bis([4-(5-[8-acryloyloxyoctyloxy]pyrimidin-2-yl)phenyl]methoxy)benzonitrile.

The 4-(5-[8-acryloyloxyoctyloxy]pyrimidin-2-yl)benzyl alcohol used as the starting material was prepared as follows:

A mixture of 0.3 g of sodium borohydride and 30 ml of water was treated dropwise at 20° C. with a solution of 1.6 g of 4-(5-[8-acryloyloxyoctyloxy]pyrimidin-2-yl)benzyl aldehyde in 100 ml of dioxan. The reaction mixture was stirred at 20° C. for 60 minutes and then at room temperature for 10 minutes, poured into 100 ml of dichloromethane and washed twice with 100 ml of water each time. The aqueous phases were combined and extracted twice with 50 ml of dichloromethane each time. The organic phases were combined, washed twice with 100 ml of water each time, dried over magnesium sulphate, the suspension was filtered and the filtrate was concentrated. This gave 1:1 g of 4-(5-[8-acryloyloxyoctyloxy]pyrimidin-2-yl)benzyl alcohol.

The following compounds can be prepared in an analogous manner:

3,4-bis([4-(5-[3-Acryloyloxypropyloxy]pyrimidin-2-yl)-phenyl]methoxy)benzonitrile;

3,4-bis([4-(5-[4-acryloyloxybutoxy]pyrimidin-2-yl)phenyl]methoxy)benzonitrile;

3,4-bis([4-(5-[5-acryloyloxypentyloxy]pyrimidin-2-yl)-phenyl]methoxy)benzonitrile;

3,4-bis([4-(5-[6-acryloyloxyhexyloxy]pyrimidin-2-yl)-phenyl]methoxy)benzonitrile;

3,4-bis([4-(5-[7-acryloyloxyheptyloxy]pyrimidin-2-yl)-phenyl]methoxy)benzonitrile;

3,4-bis([4-(5-[8-acryloyloxyoctyloxy]pyrimidin-2-yl)-phenyl]methoxy)benzonitrile;

3,4-bis([4-(5-[9-acryloyloxynonyloxy]pyrimidin-2-yl)-phenyl]methoxy)benzonitrile;

3,4-bis([4-(5-[10-acryloyloxydecyloxy]pyrimidin-2-yl)-phenyl]methoxy)benzonitrile;

3,4-bis([4-(5-[11-acryloyloxyundecyloxy]pyrimidin-2-yl)-phenyl]methoxy)benzonitrile;

3,4-bis([4-(5-[12-acryloyloxydodecyloxy]pyrimidin-2-yl)-phenyl]methoxy)benzonitrile;

methyl 3,4-bis([4-(5-[12-acryloyloxydodecyloxy]pyrimidin-2-yl)phenyl]methoxy)benzoate;

ethyl 3,4-bis([4-(5-[12-acryloyloxydodecyloxy]pyrimidin-2-yl)phenyl]methoxy)benzoate;

propyl 3,4-bis([4-(5-[12-acryloyloxydodecyloxy]pyrimidin-2-yl)phenyl]methoxy)benzoate;

3,4-bis[4-(5-[12-acryloyloxydodecyloxy]pyrimidin-2-yl)-phenyl]methoxy)toluene;

3,4-bis([4-(5-[12-acryloyloxydodecyloxy]pyrimidin-2-yl)-phenyl]methoxy)-1-ethylbenzene;

3,4-bis([4-(5-[12-acryloyloxydodecyloxy]pyrimidin-2-yl)-phenyl]methoxy)-1-propylbenzene;

3,4-bis([4-(5-[8-acryloyloxyoctyloxy]pyridin-2-yl)phenyl]-methoxy)benzonitrile;

3,4-bis([2-(4-[3-acryloyloxypropyloxy]phenyl)pyridin-5-yl]methoxy)benzonitrile;

3,4-bis([2-(4-[4-acryloyloxybutyloxy]phenyl)pyridin-5-yl]methoxy)benzonitrile;

3,4-bis([2-(4-[5-acryloyloxypentyloxy]phenyl)pyridin-5-yl]methoxy)benzonitrile;

3,4-bis([2-(4-[6-acryloyloxyhexyloxy]phenyl)pyridin-5-yl]methoxy)benzonitrile;

3,4-bis([2-(4-[7-acryloyloxyheptyloxy]phenyl)pyridin-5-yl]methoxy)benzonitrile;

3,4-bis([2-(4-[8-acryloyloxyoctyloxy]phenyl)pyridin-5-yl]methoxy)benzonitrile;

3,4-bis([2-(4-[9-acryloyloxynonyloxy]phenyl)pyridin-5-yl]methoxy)benzonitrile;

3,4-bis([2-(4-[10-acryloyloxydecyloxy]phenyl)pyridin-5-yl]methoxy)benzonitrile;

3,4-bis([2-(4-[11-acryloyloxyundecyloxy]phenyl)pyridin-5-yl]methoxy)benzonitrile;

3,4-bis([2-(4-[12-acryloyloxydodecyloxy]phenyl)pyridin-5-yl]methoxy)benzonitrile;

methyl 3,4-bis([2-(4-[8-acryloyloxyoctyloxy]phenyl)
   pyridin-5-yl]methoxy)benzoate;
ethyl 3,4-bis([2-(4-[8-acryloyloxyoctyloxy]phenyl)
   pyridin-5-yl]methoxy)benzoate;
propyl 3,4-bis([2-(4-[8-acryloyloxyoctyloxy]phenyl)
   pyridin-5-yl]methoxy)benzoate;
3,4-bis([2-(4-[8-acryloyloxyoctyloxy]phenyl)pyridin-5-
   yl]-methoxy)toluene;
3,4-bis([2-(4-[8-acryloyloxyoctyloxy]phenyl)pyridin-5-
   yl]-methoxy)-1-ethylbenzene;
3,4-bis([2-(4-[8-acryloyloxyoctyloxy]phenyl)pyridin-5-
   yl]-methoxy)-1-propylbenzene;
3,4-bis[4-(3-acryloyloxypropyloxy)biphenyl-4'-methoxy]
   -benzonitrile;
3,4-bis[4-(4-acryloyloxybutyloxy)biphenyl-4'-methoxy]
   benzonitrile;
3,4-bis[4-(5-acryloyloxypentyloxy)biphenyl-4'-methoxy]
   -benzonitrile;
3,4-bis[4-(6-acryloyloxyhexyloxy)biphenyl-4'-methoxy]-
   benzonitrile;
3,4-bis[4-(7-acryloyloxyheptyloxy)biphenyl-4'-methoxy]
   -benzonitrile;
3,4-bis[4-(8-acryloyloxyoctyloxy)biphenyl-4'-methoxy]
   benzonitrile;
3,4-bis[4-(9-acryloyloxynonyloxy)biphenyl-4'-methoxy]-
   benzonitrile;
3,4-bis[4-(10-acryloyloxydecyloxy)biphenyl-4'-
   methoxy]-benzonitrile;
3,4-bis[4-(11-acryloyloxyundecyloxy)biphenyl-4'-
   methoxy]-benzonitrile;
3,4-bis[4-(12-acryloyloxydodecyloxy)biphenyl-4'-
   methoxy]-benzonitrile;
methyl 3,4-bis[4-(8-acryloyloxyoctyloxy)biphenyl-4'-
   methoxy]-benzoate;
ethyl 3,4-bis[4-(8-acryloyloxyoctyloxy)biphenyl-4'-
   methoxy]benzoate;
propyl 3,4-bis[4-(8-acryloyloxyoctyloxy)biphenyl-4'-
   methoxy]benzoate;
3,4-bis[4-(8-acryloyloxyoctyloxy)biphenyl-4'-methoxy]
   toluene;
3,4-bis[4-(8-acryloyloxyoctyloxy)biphenyl-4'-methoxy]-
   1-ethylbenzene;
3,4-bis[4-(8-acryloyloxyoctyloxy)biphenyl-4'-methoxy]-
   1-propylbenzene;

EXAMPLE 6

0.9 g of triethylamine and then 0.5 g of methanesulphonyl chloride were added dropwise at −25° C. while stirring to a solution of 2.0 g of trans-4-(trans-4-[3-acryloyloxypropyl] cyclohexyl)-cyclohexanecarboxylic acid and 40 ml of tetrahydrofuran. The reaction mixture was stirred at −25° C. for 1 hour, then treated with 0.28 g of 3,4-dihydroxybenzonitrile and 0.05 g of 4-(dimethylamino)pyridine, stirred at room temperature overnight, poured into 100 ml of water and then extracted three times with 50 ml of diethyl ether each time. The combined organic phases were washed twice with 100 ml of water each time, dried over magnesium sulphate, filtered and subsequently concentrated. Chromatographic purification of the residue on silica gel with cyclohexane/ ethyl acetate (vol. 8:2) and two-fold recrystallization from a cyclohexane/ethyl acetate mixture (vol. 8:2) of the fractions which were pure according to thin-layer chromaography gave 1.1 g of 3,4-bis[trans-4-(trans-4-[3-acryloyloxypropyl] cyclohexyl)-cyclohexanecarbonyloxy]benzonitrile.

The trans-4-(trans-4-[3-acryloyloxypropyl]cyclohexyl)- cyclohexanecarboxylic acid used as the starting material was prepared as follows:

(a). A solution of 0.3 ml of 35% hydrochloric acid and 10.0 g of methyl trans-4-(trans-4-[2-(1,3-dioxan-2-yl) ethyl]-cyclohexyl)cyclohexanecarboxylate in 100 ml of toluene was stirred at room temperature overnight and poured into 100 ml of water. The organic phase was separated, washed twice with 100 ml of water each time, dried over magnesium sulphate, the suspension was filtered and the filtrate was concentrated. This gave 7.4 g of methyl trans-4-(trans-4-[2-formylethyl] cyclohexyl)cyclohexanecarboxylate.

(b). A mixture of 1.4 g of sodium borohydride and 140 ml of water was treated dropwise at 0° C. with a solution of 7.4 g of methyl trans-4-(trans-4-[2-formylethyl] cyclohexyl)cyclohexanecarboxylate in 100ml of dioxan. The reaction mixture was stirred at 0° C. for 60 minutes and then at room temperature for 10 minutes, poured into 100 ml of dichloromethane and washed twice with 100 ml of water each time. The aqueous phases were combined, extracted twice with 50 ml of dichloromethane each time. The organic phases were combined, washed twice with 100 ml of water each time, dried over magnesium sulphate, the suspension was filtered and the filtrate was concentrated. This gave 6.3 g of methyl trans-4-(trans-4-[3-hydroxypropyl] cyclohexyl)cyclohexanecarboxylate.

(c). A solution of 2.0 g of potassium hydroxide, 20 ml of water and 6.3 g of methyl trans-4-(trans-4-[3-hydroxypropyl]cyclohexyl)cyclohexanecarboxylate in 100 ml of ethyl alcohol was heated under slight reflux for 2 hours, poured into 100 ml of water and acidified with 25% hydrochloric acid. The precipitate was filtered off, washed portionwise with water and dried. This gave 5.2 g of trans-4-(trans-4-[3-hydroxypropyl] cyclohexyl)cyclohexanecarboxylic acid.

(d). 4.2 g of N,N'-dicyclohexylcarbodiimide were added within 5 minutes while stirring to a solution of 5.2 g of trans-4-(trans-4-[3-hydroxypropyl]cyclohexyl) cyclohexanecarboxylic acid, 1.2 g of acrylic acid and 0.2 g 4-(dimethylamino)pyridine in 25 ml of dichloromethane. The reaction mixture was stirred overnight, filtered and then concentrated. Chromatography of the residue on silica gel with hexane/ethyl acetate (vol. 8:2) and recrystallization from ethyl alcohol of the fractions which were pure according to thin-layer chromatography gave 4.2 g of trans-4-(trans-4-[3-acryloyloxypropyl]cyclohexyl)cyclohexanecarboxylic acid.

The following compounds can be prepared in an analogous manner:

3,4-bis[trans-4-(trans-4-[3-Acryloyloxypropyl]
   cyclohexyl)-cyclohexanecarbonyloxy]-2-
   fluorobenzonitrile;
3,4-bis[trans-4-(trans-4-[3-acryloyloxypropyl]
   cyclohexyl)-cyclohexanecarbonyloxy]-1-fluorobenzene;
3,4-bis[trans-4-(trans-4-[3-acryloyloxypropyl]
   cyclohexyl)cyclohexanecarbonyloxy]-1-
   chlorobenzene;
3,4-bis[trans-4-(trans-4-[3-acryloyloxypropyl]
   cyclohexyl)-cyclohexanecarbonyloxy]-1-
   bromobenzene;
3,4-bis[trans-4-(trans-4-[3-acryloyloxypropyl]
   cyclohexyl)-cyclohexanecarbonyloxy]toluene;
3,4-bis[trans-4-(trans-4-[3-acryloyloxypropyl]
   cyclohexyl)-cyclohexanecarbonyloxy]-1-
   ethylbenzene;

3,4-bis[trans-4-(trans-4-[3-acryloyloxypropyl] cyclohexyl)-cyclohexanecarbonyloxy]-1-propylbenzene;

methyl 3,4-bis[trans-4-(trans-4-[3-acryloyloxypropyl] cyclohexyl)cyclohexanecarbonyloxy]benzoate;

ethyl 3,4-bis[trans-4-(trans-4-[3-acryloyloxypropyl] cyclohexyl)cyclohexanecarbonyloxy]benzoate;

propyl 3,4-bis[trans-4-(trans-4-[3-acryloyloxypropyl] cyclohexyl)cyclohexanecarbonyloxy]benzoate;

3,4-bis[trans-4-(2-[trans-4-(3-acryloyloxypropyl) cyclohexyl]ethyl)cyclohexanecarbonyloxy] benzonitrile;

methyl 3,4-bis[trans-4-(2-[trans-4-(3-acryloyloxypropyl)-cyclohexyl]ethyl)cyclohexanecarbonyloxy]benzoate;

ethyl 3,4-bis[trans-4-(2-[trans-4-(3-acryloyloxypropyl)-cyclohexyl]ethyl)cyclohexanecarbonyloxy]benzoate;

3,4-bis[4-(trans-4-[3-acryloyloxypropyl]cyclohexyl) phenylcarbonyloxy]benzonitrile;

3,4-bis[4-(trans-4-[3-acryloyloxypropyl]cyclohexyl) phenylcarbonyloxy]-2-fluorobenzonitrile;

3,4-bis[4-(trans-4-[3-acryloyloxypropyl]cyclohexyl) phenylcarbonyloxy]-1-fluorobenzene;

3,4-bis[4-(trans-4-[3-acryloyloxypropyl]cyclohexyl) phenylcarbonyloxy]-1-chlorobenzene;

3,4-bis[4-(trans-4-[3-acryloyloxypropyl]cyclohexyl) phenylcarbonyloxy]-1-bromobenzene;

3,4-bis[4-(trans-4-[3-acryloyloxypropyl]cyclohexyl) phenylcarbonyloxy]toluene;

3,4-bis[4-(trans-4-[3-acryloyloxypropyl]cyclohexyl) phenylcarbonyloxy]-1-ethylbenzene;

3,4-bis[4-(trans-4-[3-acryloyloxypropyl]cyclohexyl) phenylcarbonyloxy]-1-propylbenzene;

methyl 3,4-bis[4-(trans-4-[3-acryloyloxypropyl] cyclohexyl)phenylcarbonyloxy]benzoate;

ethyl 3,4-bis[4-(trans-4-[3-acryloyloxypropyl] cyclohexyl)phenylcarbonyloxy]benzoate;

propyl 3,4-bis[4-(trans-4-[3-acryloyloxypropyl] cyclohexyl)phenylcarbonyloxy]benzoate;

3,4-bis[4-(2-[trans-4-(3-acryloyloxypropyl)cyclohexyl]-ethyl)phenylcarbonyloxy]benzonitrile;

methyl 3,4-bis[4-(2-[trans-4-(3-acryloyloxypropyl) cyclohexyl]ethyl)phenylcarbonyloxy]benzoate;

ethyl 3,4-bis[4-(2-[trans-4-(3-acryloyloxypropyl) cyclohexyl]ethyl)phenylcarbonyloxy]benzoate.

EXAMPLE 7

A solution of 0.433 g of N-ethyl-N'-(3-dimethylaminopropyl)carbodiimide hydrochloride (EDC) in 5 ml of dichloromethane was slowly added dropwise at 20° C. to a solution of 1.00 g of 6-[4'-[trans-4-(2-carboxy-ethyl)-cyclohexyl]-biphenyl-4-yloxy]-hexyl acrylate, 0.127 g of 3,4-dihydroxybenzonitrile and 0.255 g of 4-dimethylamino-pyridine (DMAP) in 30 ml of dichloromethane, the mixture was stirred at room temperature overnight, poured into 50 ml of water and then extracted three times with 25 ml of diethyl ether each time. The combined organic phases were washed twice with 50ml of water each time, dried over magnesium sulphate, filtered and subsequently concentrated. Chromatographic purification of the residue on silica gel with cyclohexane/ethyl acetate (vol. 8:2) and two-fold recrystallization from a cyclohexane/ethyl acetate mixture (vol. 8:2) of the fractions which were pure according to thin-layer chromatography gave 0.48 g of 3,4-bis-[3-[trans-4-[4'-(6-acryloyloxy-hexyloxy)-biphenyl-4-yl]-cyclohexyl]-propionyloxy]-benzonitrile.

The 6-[4'-[trans-4-(2-carboxy-ethyl)-cyclohexyl]-biphenyl-4-yloxy]-hexyl acrylate used as the starting material was prepared as follows:

(a). A solution of 5.238 g of dihydroxy-[4-(6-hydroxy-hexyloxy)-phenyl]-borane, 8.206 g of 4-[trans-4-(2-[1, 3]dioxolan-2-yl-ethyl)-cyclohexyl]-phenyl trifluoromethanesulphonate, 6.368 g of tripotassium phosphate, 2.619 g of potassium bromide and 0.578 g of tetrakis-(triphenylphosphine)-palladium in 100 ml of dioxan was stirred overnight at 85° C. under nitrogen. After cooling the solution was diluted with 100 ml of ether, washed three times with 50 ml of water each time, dried over magnesium sulphate, filtered and concentrated. The residue was purified by column chromatography on silica gel with cyclohexane/ethyl acetate (vol. 8:2). This gave 6.2 g of 6-[4'-[trans-4-(2-[1,3]dioxolan-2-yl-ethyl)cyclohexyl]-biphenyl-4-yloxy]-hexan-1-ol.

(b). 3.38 g of dicyclohexylcarbodiimide in 5 ml of dichloromethane was added dropwise while stirring at 0°–5° C. within 5 minutes to a solution of 6.2 g of 6-[4'-[trans-4-(2-[1,3]dioxolan-2-yl ethyl)cyclohexyl]-biphenyl-4-yloxy]-hexan-1-ol, 1.48 g of acrylic acid and 1.67 g of 4-dimethylamino-pyridine in 50 ml of dichloromethane. The reaction mixture was stirred overnight, filtered and then concentrated. Chromatography of the residue on silica gel with cyclohexane/ ethyl acetate (vol. 8:2) gave 5.14 g of 6-[4'-[trans-4-(2-[1,3]dioxolan-2-yl-ethyl)-cyclohexyl]-biphenyl-4-yloxy]-hexyl acrylate.

(c). 5.14 g of 6-[4'-[trans-4-(2-[1,3]dioxolan-2-yl-ethyl) cyclohexyl]-biphenyl-4-yloxy]-hexyl acrylate were dissolved in 100 ml of toluene. After the addition of 50 ml of formic acid the mixture was stirred at room temperature for 4 hours. Then, the organic phase was separated and the aqueous phase was extracted twice with 50 ml of toluene. The combined organic phases were washed twice with 100 ml of water, dried over magnesium sulphate and concentrated. This gave 4.55 g of 6-[4'-[trans-4-(3-oxo-propyl)-cyclohexyl]-biphenyl-4-yloxy]-hexyl acrylate.

(d). A solution of 4.55 g of 6-[4'-[trans-4-(3-oxo-propyl) cyclohexyl]-biphenyl-4-yloxy]-hexyl acrylate in 100 ml of acetone was treated dropwise at 5° C. with 20 ml of Jones' reagent. The mixture was stirred at room temperature overnight, poured into 100 ml of water and extracted three times with 50 ml of ethyl acetate. The organic phases were combined, washed twice with 100 ml of water each time, dried over magnesium sulphate, filtered and concentrated. This gave 3.86 g of 6-[4'-[trans-4-(2-carboxy-ethyl)-cyclohexyl]-biphenyl-4-yloxy]-hexyl acrylate.

The following compounds can be prepared in an analogous manner:

3,4-Bis-[3-[trans-4-[4'-(3-acryloyloxy-propyloxy)-biphenyl-4-yl]-cyclohexyl]-propionyloxy]-benzonitrile;

3,4-bis-[3-[trans-4-[4'-(4-acryloyloxy-butyloxy)-biphenyl-4-yl]-cyclohexyl]-propionyloxy]-benzonitrile;

3,4-bis-[3-[trans-4-[4'-(5-acryloyloxy-pentyloxy)-biphenyl-4-yl]-cyclohexyl]-propionyloxy]-benzonitrile;

3,4-bis-[3-[trans-4-[4'-(6-acryloyloxy-hexyloxy)-biphenyl-4-yl]-cyclohexyl]-propionyloxy]-benzonitrile;

methyl 3,4-bis-[3-[trans-4-[4'-(6-acryloyloxy-hexyloxy)-biphenyl-4-yl]-cyclohexyl]-propionyloxy]-benzoate;

ethyl 3,4-bis-[3-[trans-4-[4'-(6-acryloyloxy-hexyloxy)-biphenyl-4-yl]-cyclohexyl]-propionyloxy]-benzoate;

propyl 3,4-bis-[3-[trans-4-[4'-(6-acryloyloxy-hexyloxy)-biphenyl-4-yl]-cyclohexyl]-propionyloxy]-benzoate;

octyl 3,4-bis-[3-[trans-4-[4'-(6-acryloyloxy-hexyloxy)-biphenyl-4-yl]-cyclohexyl]-propionyloxy]-benzoate;

3,4-bis-[3-[trans-4-[4'-(6-acryloyloxy-hexyloxy)-biphenyl-4-yl]-cyclohexyl]-propionyloxy]-benzene;

3,4-bis-[3-[trans-4-[4'-(6-acryloyloxy-hexyloxy)-biphenyl-4-yl]-cyclohexyl]-propionyloxy)-toluene;

3,4-bis-[3-[trans-4-[4'-(6-acryloyloxy-hexyloxy)-biphenyl-4-yl]-cyclohexyl]-propionyloxy]-ethylbenzene;

3,4-bis-[3-[trans-4-[4'-(6-acryloyloxy-hexyloxy)-biphenyl-4-yl]-cyclohexyl]-propionyloxy]-propylbenzene.

EXAMPLE 8

A solution of 1.50 g of 6-[4'-[trans-4-[3-(trifluoromethanesulphonyl)-propyl]-cyclohexyl]-biphenyl-4-yloxy]-hexyl acrylate and 0.155 g of 3,4-dihydroxy-benzonitrile in 25 ml of 1,2-dimethoxyethane was treated portionwise at 20° C. with 0.286 g of potassium tertiary butylate and subsequently stirred overnight at 85° C. The cooled reaction mixture was poured into 25 ml of water and then extracted three times with 20 ml of ethyl acetate. The combined organic phases were washed twice with 50 ml of water, dried over magnesium sulphate, filtered and concentrated. Chromatographic purification of the residue on silica gel with cyclohexane/ethyl acetate (vol. 8:2) and two-fold recrystallization from a cyclohexane/ethyl acetate mixture (vol. 8:2) of the fractions which were pure according to thin-layer chromatography gave 1.10 g of 3,4-bis-[3-[trans-4-[4'-(6-acryloyloxy-hexyloxy)-biphenyl-4-yl]-cyclohexyl]-propoxy]-benzonitrile.

The 6-[4'-[trans-4-[3-(trifluoromethanesulphonyl)-propyl]-cyclohexyl]-biphenyl-4-yloxy]-hexyl acrylate used as the starting material was prepared as follows:

(a). A mixture of 0.123 g of sodium borohydride and 10 ml of water was treated dropwise at 20° C. with a solution of 5.00 g of 6-[4'-[trans-4-(3-oxo-propyl)-cyclohexyl]-biphenyl-4-yloxy]-hexyl acrylate in 50 ml of dioxan. The mixture was subsequently stirred at room temperature for 1 hour. The reaction mixture was poured into 50 ml of water, the phases were separated and the aqueous phase was extracted twice with 25 ml of ethyl acetate each time. The combined organic phases were washed twice with 50 ml of water each time, dried over magnesium sulphate, filtered and concentrated. Chromatographic purification of the residue on silica gel with cyclohexane/ethyl acetate (vol. 8:2) gave 4.77 g of 6-[4'-[trans-4-(3-hydroxy-propyl)-cyclohexyl]-biphenyl-4-yloxy]-hexyl acrylate.

(b). 3.47 g of trifluoromethanesulphonic anhydride dissolved in 10ml of dichloromethane were added dropwise at 0° C. to a solution of 4.77 g of 6-[4'-[trans-4-(3-hydroxy-propyl)-cyclohexyl]-biphenyl-4-yloxy]-hexyl acrylate and 1.32 g of lutidine in 100 ml of dichloromethane. The reaction mixture was stirred at 0° C. for 90 minutes and subsequently poured into 100 ml of water and extracted twice with 50 ml of dichloromethane. The combined organic phases were washed twice with 50 ml of water each time, dried over magnesium sulphate and concentrated. Chromatographic purification of the residue on silica gel with cyclohexane/ethyl acetate (vol. 8:2) gave 5.09 g of [4'-[trans-4-[3-(trifluoromethanesulphonyloxy)-propyl]-cyclohexyl]-biphenyl-4-yloxy]-hexyl acrylate.

The following compounds can be prepared in an analogous manner:

3,4-Bis-[3-[trans-4-[4'-(3-acryloyloxy-propyloxy)-biphenyl-4-yl]-cyclohexyl]-propoxy]benzonitrile;

3,4-bis-[3-[trans-4-[4'-(4-acryloyloxy-butyloxy)-biphenyl-4-yl]-cyclohexyl]-propoxy]benzonitrile;

3,4-bis-[3-[trans-4-[4'-(5-acryloyloxy-pentyloxy)-biphenyl-4-yl]-cyclohexyl]-propoxy]benzonitrile;

3,4-bis-[3-[trans-4-[4'-(6-acryloyloxy-hexyloxy)-biphenyl-4-yl)-cyclohexyl]-propoxy]benzonitrile;

methyl 3,4-bis-[3-[trans-4-[4'-(6-acryloyloxy-hexyloxy)-biphenyl-4-yl]-cyclohexyl]-propoxy]benzoate;

ethyl 3,4-bis-[3-[trans-4-[4'-(6-acryloyloxy-hexyloxy)-biphenyl-4-yl]-cyclohexyl]-propoxy]benzoate;

propyl 3,4-bis-[3-[trans-4-[4'-(6-acryloyloxy-hexyloxy)-biphenyl-4-yl]-cyclohexyl]-propoxy]benzoate;

octyl 3,4-bis-[3-[trans-4-[4'-(6-acryloyloxy-hexyloxy)-biphenyl-4-yl]-cyclohexyl]-propoxy]benzoate;

3,4-bis-[3-[trans-4-[4'-(6-acryloyloxy-hexyloxy)-biphenyl-4-yl]-cyclohexyl]-propoxy]benzene;

3,4-bis-[3-[trans-4-[4'-(6-acryloyloxy-hexyloxy)-biphenyl-4-yl]-cyclohexyl]-propoxy]toluene;

3,4-bis-[3-[trans-4-[4'-(6-acryloyloxy-hexyloxy)-biphenyl-4-yl]-cyclohexyl]-propoxy]ethylbenzene;

3,4-bis-[3-[trans-4-[4'-(6-acryloyloxy-hexyloxy)-biphenyl-4-yl]-cyclohexyl]-propoxy]propylbenzene.

EXAMPLE 9

A solution of 0.418 g of N-ethyl-N'-(3-dimethylaminopropyl)carbodiimide hydrochloride (EDC) in 5 ml of dichloromethane was slowly added dropwise at 0° C. to a solution of 1.00 g of 4-[2',3'-difluoro-4"-(3-carboxy-propyl)-1,2':4',1"-terphenyl-4-yloxy]-butyl acrylate, 0.123 g of 3,4-dihydroxybenzonitrile and 0.247 g of 4-dimethylaminopyridine (DMAP) in 30 ml of dichloromethane, the mixture was stirred at room temperature overnight, poured into 50 ml of water and then extracted three times with 25 ml of diethyl ether each time. The combined organic phases were washed twice with 50 ml of water each time, dried over magnesium sulphate, filtered and subsequently concentrated. Chromatographic purification of the residue on silica gel with cyclohexane/ethyl acetate (vol. 8:2) and two-fold recrystallization from a cyclohexane/ethyl acetate mixture (vol. 8:2) of the fractions which were pure according to thin-layer chromatography gave 0.39 g of 3,4-bis-[4-[4"-(4-acryloyloxy-butoxy)-2',3'-difluoro-1,1':4',1"-terphenyl-butyryloxy]-benzonitrile.

The 4-[2',3'-difluoro-4"-(3-carboxy-propyl)-1,2':4',1"-terphenyl-4-yloxy]-butyl acrylate used as the starting material was prepared as follows:

(a). 13.0 ml of a 1.6 molar solution of butyllithium in hexane was slowly added dropwise to a solution of 5.80 g of 2-[3-(2',3'-difluorobiphenyl-4-yl)-propyl]-[1,3] dioxolane in 80 ml of dry tetrahydrofuran under nitrogen at −78° C. and the mixture was stirred at this temperature for 2.5 hours. Then, a solution of 4.32 g of trimethyl borate in 10 ml of tetrahydrofuran was added dropwise thereto. The solution was left to warm slowly and was stirred at room temperature overnight. Then, 50 ml of 10% hydrochloric acid were added thereto, the mixture was stirred for one hour, the phases were separated and extracted twice with 25 ml of ether. The combined organic phases were washed twice with 50 ml of water, dried over magnesium sulphate, filtered and concentrated. This gave 5.3 g of [2,3-difluoro-4'-(4-oxo-butyl)biphenyl-4-yl] -dihydroxy-borane.

(b). A solution of 5.30 g of [2,3-difluoro-4'-(4-oxo-butyl) biphenyl-4-yl]-dihydroxy-borane, 6.18 g of 3-(bromophenoxy)-propyl acrylate, 0.50 g of tetrakis-(triphenylphosphine)-palladium and 17.5 ml of 2M sodium carbonate solution in 100 ml of 1,2-dimethoxyethane was stirred overnight at 85° C. under nitrogen. After cooling the solution was diluted with 100 ml of ether, washed three times with 50 ml of water each time, dried over magnesium sulphate, filtered and concentrated. The residue was purified by column chromatography on silica gel with cyclohexane/ethyl acetate (vol. 8:2). This gave 5.55 g of 4-[2',3'-difluoro-4"-(4-oxo-butyl)-1,2':4',1"-terphenyl-4-yloxy]-butyl acrylate.

(c). A solution of 5.55 g of 4-[2',3'-difluoro-4"-(4-oxo-butyl)-1,2':4',1"-terphenyl-4-yloxy]-butyl acrylate in 100 ml of acetone was treated dropwise at 5° C. with 20 ml of Jones' reagent. The mixture was stirred at room temperature overnight, poured into 100 ml of water and extracted three times with 50 ml of ethyl acetate. The organic phases were combined, washed twice with 100 ml of water each time, dried over magnesium sulphate, filtered and concentrated. This gave 5.29 g of 4-[2',3'-difluoro-4"-(3-carboxy-propyl)-1,2':4',1"-terphenyl-4-yloxy]-butyl acrylate.

The following compounds can be prepared in an analogous manner:

3,4-Bis-[4-[4"-(3-acryloyloxy-propoxy)-2',3'-difluoro-1,1':4',1"-terphenyl]-butyryloxy]-benzonitrile;

3,4-bis-[4-[4"-(5-acryloyloxy-pentoxy)-2',3'-difluoro-1,1':4',1"-terphenyl]-butyryloxy]-benzonitrile;

3,4-bis-[4-[4"-(6-acryloyloxy-hexoxy)-2',3'-difluoro-1,1':4',1"-terphenyl]-butyryloxy]-benzonitrile;

methyl 3,4-bis-[4-[4"-(4-acryloyloxy-butoxy)-2',3'-difluoro-1,1':4',1"-terphenyl]-butyryloxy]-benzoate;

ethyl 3,4-bis-[4-[4"-(4-acryloyloxy-butoxy)-2',3'-difluoro-1,1':4',1"-terphenyl]-butyryloxy]-benzoate;

propyl 3,4-bis-[4-[4"-(4-acryloyloxy-butoxy)-2',3'-difluoro-1,1':4',1"-terphenyl]-butyryloxy]-benzoate;

octyl 3,4-bis-[4-[4"-(4-acryloyloxy-butoxy)-2',3'-difluoro-1,1':4',1"-terphenyl]-butyryloxy]-benzoate;

3,4-bis-[4-[4"-(4-acryloyloxy-butoxy)-2',3'-difluoro-1,1':4',1"-terphenyl]-butyryloxy]-benzene;

3,4-bis-[4-[4"-(4-acryloyloxy-butoxy)-2',3'-difluoro-1,1':4',1"-terphenyl]-butyryloxy]-toluene;

3,4-bis-[4-[4"-(4-acryloyloxy-butoxy)-2',3'-difluoro-1,1':4',1"-terphenyl]-butyryloxy]-ethylbenzene;

3,4-bis-[4-[4"-(4-acryloyloxy-butoxy)-2',3'-difluoro-1,1':4',1"-terphenyl]-butyryloxy] -propylbenzene.

EXAMPLE 10

A solution of 1.50 g of 4-[2',3'-difluoro-4"-[4-(trifluoromethanesulphonyloxy)-butyl]-1,2':4',1"-terphenyl-4-yloxy]-butyl acrylate and 0.156 g of 3,4-dihydroxybenzonitrile in 25 ml of 1,2-dimethoxyethane was treated portionwise at 0° C. with 0.292 g of potassium tertiary butylate and the mixture was subsequently stirred at 85° C. overnight. The cooled reaction mixture was poured into 25 ml of water and then extracted three times with 20 ml of ethyl acetate. The combined organic phases were washed twice with 50 ml of water, dried over magnesium sulphate, filtered and concentrated. Chromatographic purification of the residue on silica gel with cyclohexane/ethyl acetate (vol. 8:2) and two-fold recrystallization from a cyclohexane/ethyl acetate mixture (vol. 8:2) of the fractions which were pure according to thin-layer chromatography gave 0.65 g of 3,4-bis-[4-[4-(4-acryloyloxy-butoxy)-2',3'-difluoro-1,1':4',1"-terphenyl]-butoxy]benzonitrile.

The 4-[2',3'-difluoro-4"-[4-(trifluoromethanesulphonyloxy)-butyl]-1,2':4',1"-terphenyl-4-yloxy]-butyl acrylate used as the starting material was prepared as follows:

(a). A mixture of 0.119 g of sodium borohydride and 10 ml of water was treated dropwise at 0° C. with a solution of 5.00 g of 4-[2',3'-difluoro-4"-(4-oxo-butyl)-1,2':4',1"-terphenyl-4-yloxy]-butyl acrylate in 50 ml of dioxan. The mixture was subsequently stirred at room temperature for 1 hour. The reaction mixture was poured into 50 ml of water, the phases were separated and the aqueous phase was extracted twice with 25 ml of ethyl acetate each time. The combined organic phases were washed twice with 50 ml of water each time, dried over magnesium sulphate, filtered and concentrated. Chromatographic purification of the residue on silica gel with cyclohexane/ethyl acetate (vol. 8:2) gave 4.49 g of 4-[2',3'-difluoro-4"-(4-hydroxy-butyl)-1,2':4',1"-terphenyl -4-yloxy]-butyl acrylate.

(b). 3.10 g of trifluoromethanesulphonic anhydride dissolved in 10 ml of dichloromethane was added dropwise at 0° C. to a solution of 4.40 g of 4-[2',3'-difluoro-4"-(4-hydroxy-butyl)-1,2':4',1"-terphenyl-4-yloxy]-butyl acrylate and 1.18 g of lutidine in 100 ml of dichloromethane. The reaction mixture was stirred at 0° C. for 90 minutes and subsequently poured into 100 ml of water and extracted twice with 50 ml of dichloromethane. The combined organic phases were washed twice with 50 ml of water each time, dried over magnesium sulphate and concentrated. Chromatographic purification of the residue on silica gel with cyclohexane/ethyl acetate (vol. 8:2) gave 4.20 g of 4-[2',3'-difluoro-4"-[4-(trifluoromethanesulphonyloxy)-butyl]-1,2':4',1"-terphenyl-4-yloxy]-butyl acrylate.

The following compounds can be prepared in an analogous manner:

3,4-Bis-[4-[4-(3-acryloyloxy-propoxy)-2',3'-difluoro-1,1':4',1"-terphenyl]-butoxy]benzonitrile;

3,4-bis-[4-[4-(5-acryloyloxy-pentoxy)-2',3'-difluoro-1,1':4',1"-terphenyl]-butoxy]benzonitrile;

3,4-bis-[4-[4-(6-acryloyloxy-hexoxy)-2',3'-difluoro-1,1':4',1"-terphenyl]-butoxy]benzonitrile;

methyl 3,4-bis-[4-[4-(4-acryloyloxy-butoxy)-2',3'-difluoro-1,1':4',1"-terphenyl]-butoxy]benzoate;

ethyl 3,4-bis-[4-[4-(4-acryloyloxy-butoxy)-2',3'-difluoro-1,1':4',1"-terphenyl]-butoxy]benzoate;

propyl 3,4-bis-[4-[4-(4-acryloyloxy-butoxy)-2',3'-difluoro-1,1':4',1"-terphenyl]-butoxy]benzoate;

octyl 3,4-bis-[4-[4-(4-acryloyloxy-butoxy)-2',3'-difluoro-1,1':4',1"-terphenyl]-butoxy]benzoate;

3,4-bis-[4-[4-(4-acryloyloxy-butoxy)-2',3'-difluoro-1,1':4',1"-terphenyl]-butoxy]benzene;

3,4-bis-[4-[4-(4-acryloyloxy-butoxy)-2',3'-difluoro-1,1':4',1"-terphenyl]-butoxy]ethylbenzene;

3,4-bis-[4-[4-(4-acryloyloxy-butoxy)-2',3'-difluoro-1,1':4',1''-terphenyl]-butoxy]propylbenzene.

I claim:
1. A compound of the formula

$$R^1-Z^5-\left(\left(B\right)-Z^3\right)_n\left(A\right)-Z^1$$
$$R^2-Z^6-\left(\left(D\right)-Z^4\right)_m\left(C\right)-Z^2 \quad X^2 \quad X^3$$
$$X^1 \quad \left(Z^7-\left(E\right)\right)_q$$
$$\left(Z^8-\left(F\right)\right)_r R^3$$

I wherein
each of rings A,
B, C, D, E, and F independently is pyridine-2,5-diyl, pyrimidine-2,5-diyl, trans-1,4-cyclohexylene, trans-1,3-dioxane-2,5-diyl or 1,4-phenylene which is unsubstituted or substituted with one or more of halogen, methyl, or cyano;
each of $Z^1$, $Z^2$
and $Z^7$ independently is —CH$_2$—(CH$_2$)$_s$—, —(CH$_2$)$_s$O—, —O(CH$_2$)$_s$—, —COO—, —OOC—, —(CH$_2$)$_s$COO— or —(CH$_2$)$_s$OOC—;
each of $Z^3$, $Z^4$
and $Z^8$ independently is a single bond, —CH$_2$CH$_2$—, —CH$_2$O—, —OCH$_2$—, —COO—, —OOC—, —(CH$_2$)$_4$—, —O(CH$_2$)$_3$— or —(CH$_2$)$_3$O—;
each of $Z^5$
and $Z^6$ independently is —(CY$_2$)$_s$—, —O(CY$_2$)$_s$—, —(CY$_2$)$_s$O—, —(CY$_2$)$_s$COO—, —(CY$_2$)$_s$OOC—, —(Si[(CH$_3$)$_2$]O)$_s$—, —OCH$_2$(Si[(CH$_3$)$_2$]O)$_s$Si[(CH$_3$)$_2$]CH$_2$O—, or —NHCH$_2$(Si[(CH$_3$)$_2$]O)$_s$Si[(CH$_3$)$_2$]CH$_2$NH—;
Y is hydrogen or fluorine;
each of m, n,
q and r independently is 0, 1 or 2;
s is a whole number of 1 to 16;
each of $R^1$
and $R^2$ independently is CH$_2$=CH—, CH$_2$=CH—COO—, CH$_2$=C(CH$_3$)—COO—, CH$_2$=C(Cl)—COO—, CH$_2$=C(Ph)—COO—, CH$_2$=CH—COO—Ph—, CH$_2$=CH—CO—NH—, CH$_2$=C(CH$_3$)—CONH—, CH$_2$=C(Cl)—CONH—, CH$_2$=C(Ph)—CONH—, CH$_2$=C(COOR')—CH$_2$—COO—, CH$_2$=CH—O—, CH$_2$=CH—OOC—, Ph—CH=CH—, CH$_3$—C(=NR')—, cis,trans HOO—CR'=CR'—COO—,

[epoxide structure] H$_2$C—CH—, [phenyl]—CH=CH— or
          \O/

R''—[phenyl]—CH=CH—COO—

Ph is phenyl;
R' is lower alkyl;
R'' is methyl, methoxy, cyano or halogen, with the proviso that $R^1$—$Z^5$ and $R^2$—$Z^6$ contain no —O—O— or —N—O— groups;
$R^3$ is hydrogen, halogen, cyano, an alkyl, alkoxy, alkoxycarbonyl or alkanoyloxy groups, the alkyl, alkoxy, alkoxycarbonyl, or alkanoyloxy group being unsubstituted or substituted with one or more of methoxy, cyano or halogen; and
each of $X^1$, $X^2$
and $X^3$ independently is hydrogen, halogen, cyano or lower alkyl,
whereby rings B and D can be the same or different when either or both of m and n is 2.

2. The compound according to claim 1 of formula I $$R^1-Z^5-\left(\left(B\right)-Z^3\right)_n\left(A\right)-Z^1$$
$$R^2-Z^6-\left(\left(D\right)-Z^4\right)_m\left(C\right)-Z^2 \quad X^2 \quad X^3$$
$$X^1 \quad \left(Z^7-\left(E\right)\right)_q$$
$$\left(Z^8-\left(F\right)\right)_r R^3$$

I wherein
each of ring A,
B, C, D, E, and F independently is pyridine-2,5-diyl, pyrimidine-2,5-diyl, trans-1,4-cyclohexylene, trans-1,3-dioxane-2,5-diyl or 1,4-phenylene which is unsubstituted or substituted with one or more of halogen, methyl, or cyano;
each of $Z^1$, $Z^2$
and $Z^7$ is —CH$_2$CH$_2$—, —CH$_2$O—, —COO—, —OOC—, —(CH$_2$)$_4$— or —(CH$_2$)$_3$O—;
each of $Z^3$, $Z^4$
and $Z^8$ is a single bond, —CH$_2$CH$_2$—, —CH$_2$O—, —OCH$_2$—, —COO—, —OOC—, —(CH$_2$)$_4$—, —O(CH$_2$)$_3$— or —(CH$_2$)$_3$O—;
each of $Z^5$
and $Z^6$ is —(CY$_2$)$_s$—, —O(CY$_2$)$_s$—, —(CY$_2$)$_s$O—, —(CY$_2$)$_s$COO—, —(CY$_2$)$_s$OOC—, —(Si[(CH$_3$)$_2$]O)$_s$—, —OCH$_2$(Si[(CH$_3$)$_2$]O)$_s$Si[(CH$_3$)$_2$]CH$_2$O— or —NHCH$_2$(Si[(CH$_3$)$_2$]O)$_s$Si[(CH$_3$)$_2$]CH$_2$NH—;
Y is hydrogen or fluorine;
each of m, n,
q and r independently is 0 or 1;
s is a whole number of 1 to 16;
each of $R^1$
and $R^2$ is CH$_2$=CH—, CH$_2$=CH—COO—, CH$_2$=C(CH$_3$)—COO—, CH$_2$=C(Cl)—COO—, CH$_2$=C(Ph)—COO—, CH$_2$=CH—COO—Ph—, CH$_2$=CH—CO—NH—, CH$_2$=C(CH$_3$)—CONH—, CH$_2$=C(Cl)—CONH—, CH$_2$=C(Ph)—CONH—, CH$_2$=C(COOR')—CH$_2$—COO—, CH$_2$=CH—O—, CH$_2$=CH—OOC—, Ph—CH=CH—, CH$_3$—C(=NR')—, cis,trans HOO—CR'=CR'—COO—,

[epoxide structure] H$_2$C—CH—, [phenyl]—CH=CH— or
          \O/

R''—[phenyl]—CH=CH—COO—

Ph is phenyl;
R' is lower alkyl;
R'' is methyl, methoxy, cyano or halogen, with the proviso that $R^1$—$Z^5$ and $R^2$—$Z^6$ contain no —O—O— or —N—O— groups;

$R^3$ is hydrogen, halogen, cyano or an alkyl, alkoxy or alkanoyloxy group, the alkyl, alkoxy, or alkanolyloxy group being unsubstituted or substituted with one or more of methoxy, cyano, or halogen; and each is $X^1$, $X^2$ and $X^3$ is hydrogen, halogen, cyano or lower alkyl.

3. The compound according to claim 1 wherein each of $R^1$ and $R^2$ is $CH_2=CH-COO-$, $CH_2=C(CH_3)-COO-$, $CH_2=CH-O-$, or

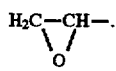

4. The compound according to claim 3 wherein each of $X^1$, $X^2$, and $X^3$ is hydrogen, fluorine, chlorine, cyano, or methyl.

5. The compound according to claim 2, wherein each of $R^1$ and $R^2$ is $CH_2=CH-COO-$, $CH_2=C(CH_3)-COO-$, $CH_2=CH-O-$ or

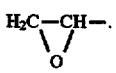

6. The compound according to claim 5 wherein each of $X^1$, $X^2$ and $X^3$ is hydrogen, fluorine, chlorine, cyano, or methyl.

7. A compound of the formula IA $Z^{11}$ is $-CH_2CH_2-$, $-CH_2O-$, $-COO-$, $-OOC-$, $-(CH_2)_4-$ or $-(CH_2)_3O-$;

$Z^{31}$ is a single bond, $-CH_2O-$, $-COO-$ or $-OOC-$;

$Z^{51}$ is $-(CH_2)_{s'}-$, $-(CH_2)_{s'}O-$, $-(CH_2)_{s'}COO-$ or $-(CH_2)_{s'}OOC-$;

$Z^{71}$ is $-CH_2O-$ or $-COO-$;

$s'$ is a whole number of 3 to 12;

$R^{11}$ is $CH_2=CH-COO-$, $CH_2=C(CH_3)-COO-$, $CH_2=CH-O-$ or 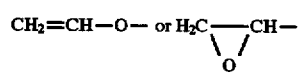

$R^{31}$ is halogen, cyano, lower alkyl or alkoxycarbonyl;

q is 0 or 1; and each of $X^1$, $X^2$ and $X^3$ independently is hydrogen, halogen, cyano or lower alkyl.

8. The compound according to claim 7 of formula Ia

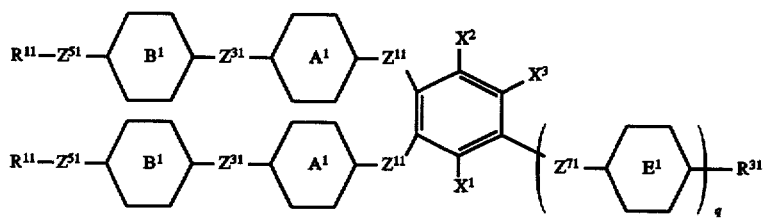

I-A

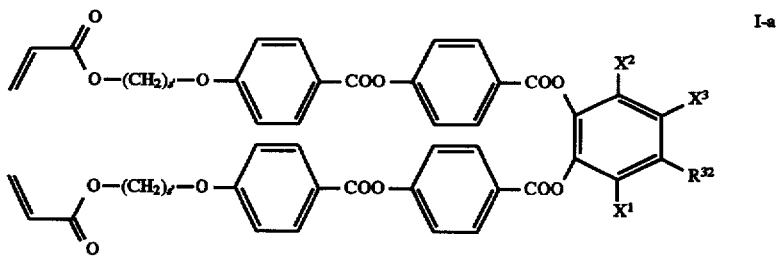

I-a wherein each of $A^1$, $B^1$ and $E^1$ independently is 1,4-phenylene unsubstituted or substituted with fluorine; pyridine-2,5-diyl, pyrimidine-2,5—diyl or trans-1,4-cyclohexylene;

wherein $R^{32}$ is cyano or alkoxycarbonyl and each of $X^1$, $X^2$, and $X^3$ is hydrogen.

9. The compound according to claim 7 of formula I-b

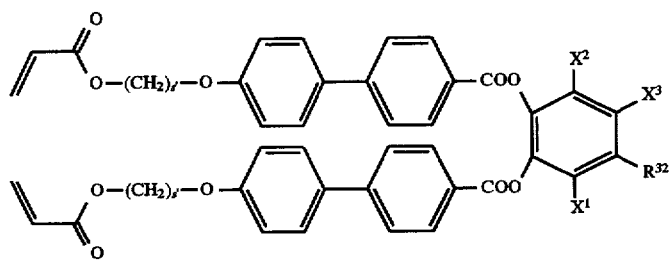

wherein
R³² is cyano or alkoxycarbonyl and each of X¹, X², and X³ is hydrogen.

10. The compound according to claim 7 of formula I-C

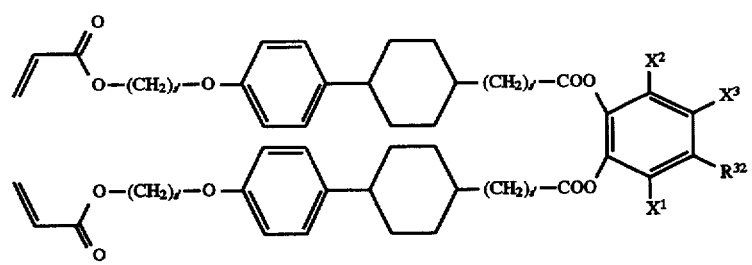

wherein
R³² is cyano or alkoxycarbonyl and each of X¹, X², and X³ is hydrogen.

11. A compound of the formula I-B

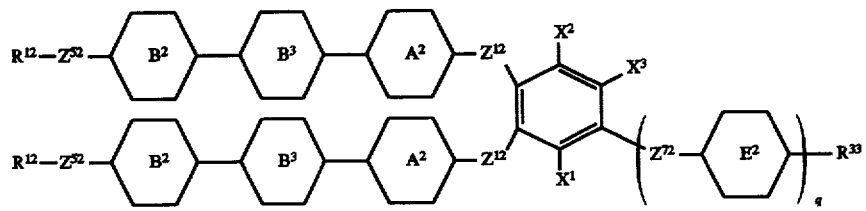

wherein
each of A², B², B³ and E² independently is 1,4-phenylene unsubstituted or substituted with fluorine or trans-1,4-cyclohexylene;
$Z^{12}$ is —(CH$_2$)$_2$COO—, —(CH$_2$)$_{s'}$COO— or —(CH$_2$)$_{s'}$O—;
$Z^{52}$ is —(CH$_2$)$_{s'}$—, —(CH$_2$)$_{s'}$O—, —(CH$_2$)$_{s'}$COO— or —(CH$_2$)$_{s'}$OOC—;
$Z^{72}$ is —CH$_2$O— or —COO—;
s' a whole number of 3 to 12;

$R^{12}$ is CH$_2$=CH—COO—, CH$_2$=C(CH$_3$)—COO—,

CH$_2$=CH—O— or H$_2$C—CH—
\\O/

R³³ is halogen, cyano or alkoxycarbonyl;
q is 0 or 1; and
each of X¹, X² and X³ independently is hydrogen, halogen, cyano, or lower alkyl.

12. The compound according to claim 11 of formula Id

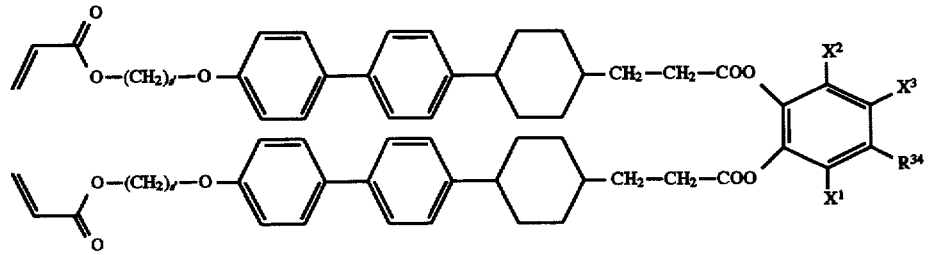

wherein

R³⁴ is cyano or alkoxycarbonyl and each of X¹, X² and X³ is hydrogen.

13. The compound according to claim 11 of formula I-e

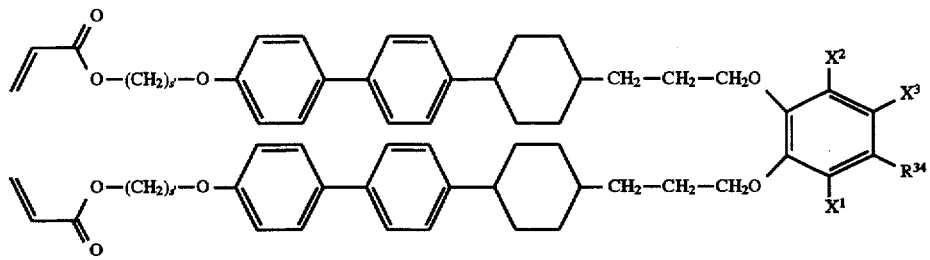

I-e wherein

R³⁴ is cyano or alkoxycarbonyl and each of X¹, X² and X³ is hydrogen.

14. The compound according to claim 11 of formula I-f

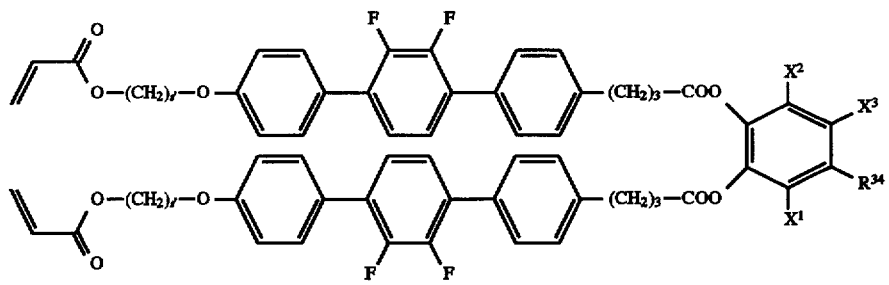

I-f wherein

R³⁴ is cyano or alkoxycarbonyl and each of X¹, X² and X³ is hydrogen.

15. The compound according to claim 11 of formula I-g

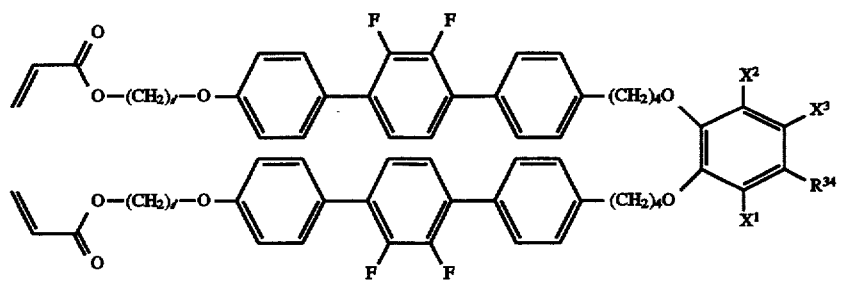

I-g wherein

R³⁴ is cyano or alkoxycarbonyl and each of X¹, X² and X³ is hydrogen.

16. A cross-linkable liquid crystalline mixture having two components, wherein at least one component is a compound of the formula

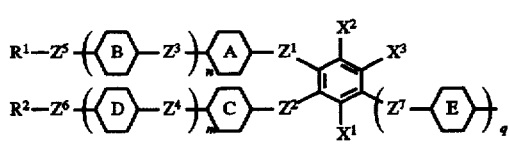

I

-continued

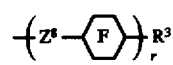

wherein
each of rings A,
B, C, D, E, and F independently is pyridine-2,5-diyl, pyrimidine-2,5-diyl, trans-1,4-cyclohexylene, trans-1,3-dioxane-2,5-diyl or 1,4-phenylene which is unsubstituted or substituted with one or more of halogen, methyl, or cyano;
each of $Z^1$, $Z^2$ and $Z^7$ independently is —CH₂—(CH₂)ₛ—, —(CH₂)ₛO—, —O(CH₂)ₛ—, —COO—, —OOC—, —(CH₂)ₛCOO— or —(CH₂)ₛOOC—;

each of $Z^3$, $Z^4$ and $Z^8$ independently is a single bond, —CH$_2$CH$_2$—, —CH$_2$O—, —OCH$_2$—, —COO—, —OOC—, —(CH$_2$)$_4$—, —O(CH$_2$)$_3$— or —(CH$_2$)$_3$O—;

each of $Z^5$ and $Z^6$ independently is —(CY$_2$)$_s$—, —O(CY$_2$)$_s$—, —(CY$_2$)$_s$O—, —(CY$_2$)$_s$COO—, —(CY$_2$)$_s$OOC—, —(Si[(CH$_3$)$_2$]O)$_s$—, —OCH$_2$(Si[(CH$_3$)$_2$]O)$_s$Si[(CH$_3$)$_2$]CH$_2$O—, or —NHCH$_2$(Si[(CH$_3$)$_2$]O)$_s$Si[(CH$_3$)$_2$]CH$_2$NH—;

Y is hydrogen or fluorine;

each of m, n, q and r independently is 0, 1 or 2;

s is a whole number of 1 to 16;

each of $R^1$ and $R^2$ independently is CH$_2$=CH—, CH$_2$=CH—COO—, CH$_2$=C(CH$_3$)—COO—, CH$_2$=C(Cl)—COO—, CH$_2$=C(Ph)—COO—, CH$_2$=CH—COO—Ph—, CH$_2$=CH—CO—NH—, CH$_2$=C(CH$_3$)—CONH—, CH$_2$=C(Cl)—CONH—, CH$_2$=C(Ph)—CONH—, CH$_2$=C(COOR')—CH$_2$—COO—, CH$_2$=CH—O—, CH$_2$=CH—OOC—, Ph—CH=CH—, CH$_3$—C(=NR')—, cis,trans HOO—CR'=CR'—COO—,

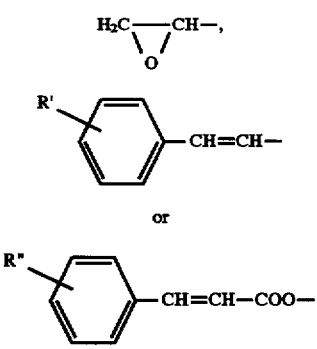

Ph is phenyl;

R' is lower alkyl;

R" is methyl, methoxy, cyano or halogen, with the proviso that $R^1$—$Z^5$ and $R^2$—$Z^6$ contain no —O—O— or —N—O— groups;

$R^3$ is hydrogen, halogen, cyano, an alkyl, alkoxy, alkoxycarbonyl or alkanoyloxy groups, the alkyl, alkoxy, alkoxycarbonyl, or alkanoyloxy group being unsubstituted or substituted with one or more of methoxy, cyano or halogen; and each of $X^1$, $X^2$ and $X^3$ independently is hydrogen, halogen, cyano or lower alkyl, whereby rings B and D can be the same or different when either or both of m and n is 2.

17. A cross-linkable liquid crystalline mixture comprising a compound of formula I

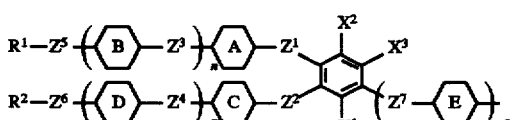

-continued

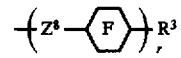

wherein each of rings A,

B, C, D, E, and F independently is pyridine-2,5-diyl, pyrimidine-2,5-diyl, trans-1,4-cyclohexylene, trans-1,3-dioxane-2,5-diyl or 1,4-phenylene which is unsubstituted or substituted with one or more of halogen, methyl, or cyano;

each of $Z^1$, $Z^2$ and $Z^7$ independently is —CH$_2$—(CH$_2$)$_s$—, —(CH$_2$)$_s$O—, —O(CH$_2$)$_s$—, —COO—, —OOC—, —(CH$_2$)$_s$COO— or —(CH$_2$)$_s$OOC—;

each of $Z^3$, $Z^4$ and $Z^8$ independently is a single bond, —CH$_2$CH$_2$—, —CH$_2$O—, —OCH$_2$—, —COO—, —OOC—, —(CH$_2$)$_4$—, —O(CH$_2$)$_3$— or —(CH$_2$)$_3$O—;

each of $Z^5$ and $Z^6$ independently is —(CY$_2$)$_s$—, —O(CY$_2$)$_s$—, —(CY$_2$)$_s$O—, —(CY$_2$)$_s$COO—, —(CY$_2$)$_s$OOC—, —(Si[(CH$_3$)$_2$]O)$_s$—, —OCH$_2$(Si[(CH$_3$)$_2$]O)$_s$Si[(CH$_3$)$_2$]CH$_2$O—, or —NHCH$_2$(Si[(CH$_3$)$_2$]O)$_s$Si[(CH$_3$)$_2$]CH$_2$NH—;

Y is hydrogen or fluorine;

each of m, n, q and r independently is 0, 1 or 2;

s is a whole number of 1 to 16;

each of $R^1$ and $R^2$ independently is CH$_2$=CH—, CH$_2$=CH—COO—, CH$_2$=C(CH$_3$)—COO—, CH$_2$=C(Cl)—COO—, CH$_2$=C(Ph)—COO—, CH$_2$=CH—COO—Ph—, CH$_2$=CH—CO—NH—, CH$_2$=C(CH$_3$)—CONH—, CH$_2$=C(Cl)—CONH—, CH$_2$=C(Ph)—CONH—, CH$_2$=C(COOR')—CH$_2$—COO—, CH$_2$=CH—O—, CH$_2$=CH—OOC—, Ph—CH=CH—, CH$_3$—C(=NR')—, cis,trans HOO—CR'=CR'—COO—,

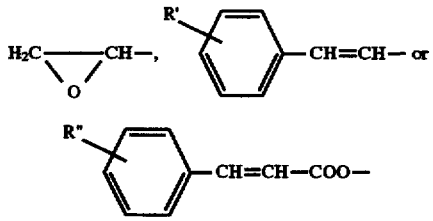

Ph is phenyl;

R' is lower alkyl;

R" is methyl, methoxy, cyano or halogen, with the proviso that $R^1$—$Z^5$ and $R^2$—$Z^6$ contain no —O—O— or —N—O — groups;

$R^3$ is hydrogen, halogen, cyano, an alkyl, alkoxy, alkoxycarbonyl or alkanoyloxy groups, the alkyl, alkoxy, alkoxycarbonyl, or alkanoyloxy group being unsubstituted or substituted with one or more of methoxy, cyano or halogen; and each of $X^1$, $X^2$ and $X^3$ independently is hydrogen, halogen, cyano or lower alkyl, whereby rings B and D can be the same or different when either or both of m and n is 2 and one or more compounds selected from the group consisting of the formulae

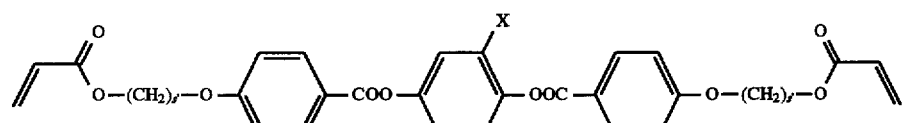
II
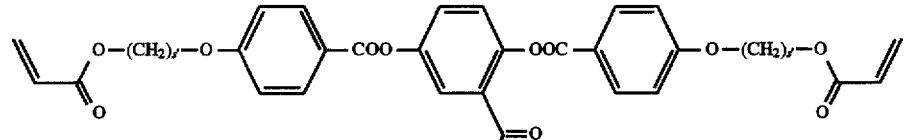
III
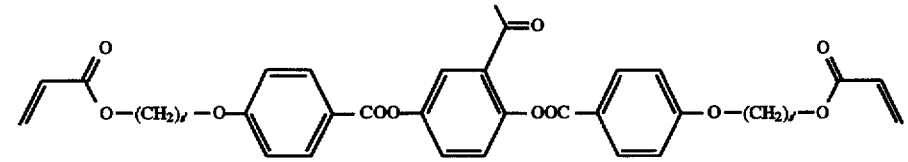
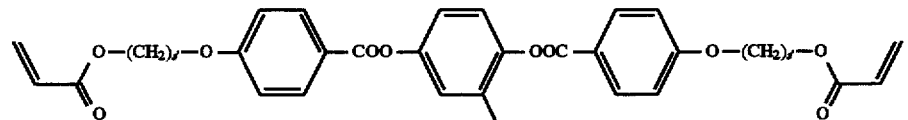
IV
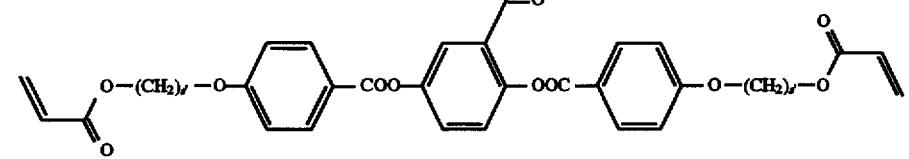
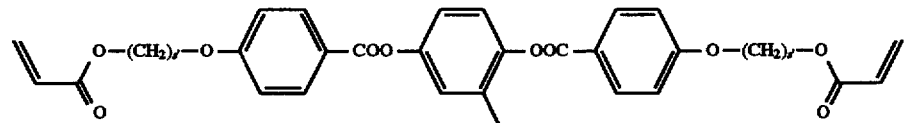
V
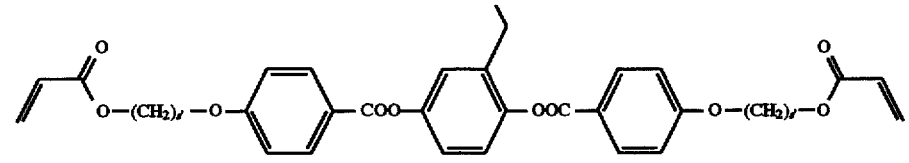

-continued

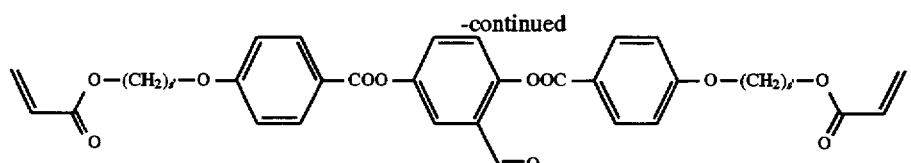

VI

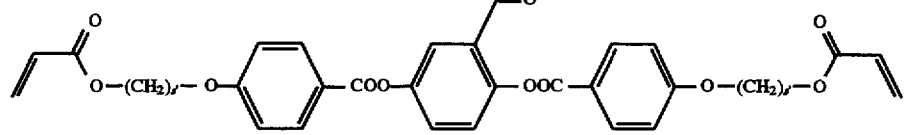

VII

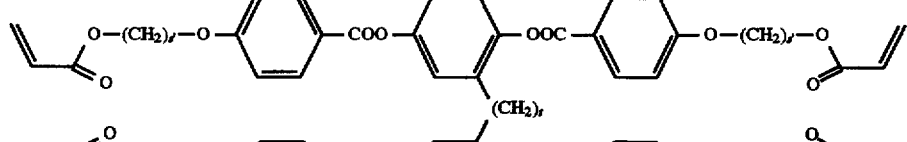

VIII

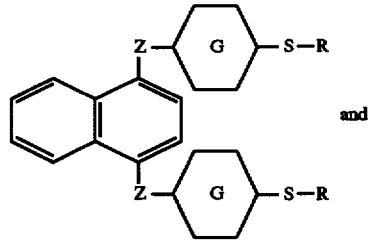

and

IX

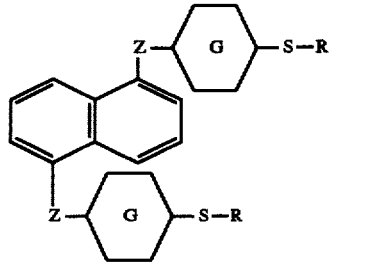

wherein

X is hydrogen, fluorine, chlorine, bromine or methyl;
s' is a whole number of 3 to 12; and
t is a whole number of 2 to 12;
Z is —OCH$_2$— or —OOC—;
G is 1,4-phenylene or 2- or 3-fluoro-1,4-phenylene;
S is —(CH$_2$)$_s$'— or —(CH$_2$)$_s$O—; and
R is CH$_2$=CH—COO—, CH$_2$=C(CH$_3$)—COO—,

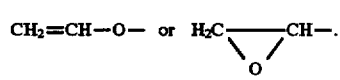

18. An electro-optical cell comprising
(a) two plate means;
(b) liquid crystal means disposed between the two plate means and including a compound of formula I

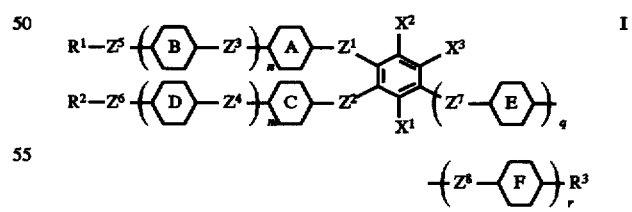

I wherein
each of rings A,
B, C, D, E, and F independently is pyridine-2,5-diyl, pyrimidine-2,5-diyl, trans-1,4-cyclohexylene, trans-1,3-dioxane-2,5-diyl or 1,4-phenylene which is unsubstituted or substituted with one or more of halogen, methyl, or cyano;
each of $Z^1$, $Z^2$ and $Z^7$ independently is —$CH_2$—$(CH_2)_s$—, —$(CH_2)_sO$—, —$O(CH_2)_s$—, —COO—, —OOC—, —$(CH_2)_sCOO$— or —$(CH_2)_sOOC$—;

each of $Z^3$, $Z^4$ and $Z^8$ independently is a single bond, —$CH_2CH_2$—, —$CH_2O$—, —$OCH_2$—, —COO—, —OOC—, —$(CH_2)_4$—, —$O(CH_2)_3$— or —$(CH_2)_3O$—;

each of $Z^5$ and $Z^6$ independently is —$(CY_2)_s$—, —$O(CY_2)_s$—, —$(CY_2)_sO$—, —$(CY_2)_sCOO$—, —$(CY_2)_sOOC$—, —$(Si[(CH_3)_2]O)_s$—, —$OCH_2(Si[(CH_3)_2]O)_sSi[(CH_3)_2]CH_2O$—, or —$NHCH_2(Si[(CH_3)_2]O)_sSi[(CH_3)_2]CH_2NH$—;

Y is hydrogen or fluorine;

each of m, n, q and r independently is 0, 1 or 2;

s is a whole number of 1 to 16;

each of $R^1$ and $R^2$ independently is $CH_2$=CH—, $CH_2$=CH—COO—, $CH_2$=C($CH_3$)—COO—, $CH_2$=C(Cl)—COO—, $CH_2$=C(Ph)—COO—, $CH_2$=CH—COO—Ph—, $CH_2$=CH—CO—NH—, $CH_2$=C($CH_3$)—CONH—, $CH_2$=C(Cl)—CONH—, $CH_2$=C(Ph)—CONH—, $CH_2$=C(COOR')—$CH_2$—COO—, $CH_2$=CH—O—, $CH_2$=CH—OOC—, Ph—CH=CH—, $CH_3$—C(=NR')—, cis,trans HOO—CR'=CR'—COO—,

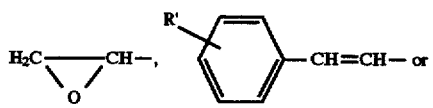

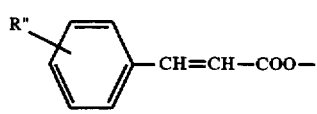

Ph is phenyl;

R' is lower alkyl;

R" is methyl, methoxy, cyano or halogen, with the proviso that $R^1$—$Z^5$ and $R^2$—$Z^6$ contain no —O—O— or —N—O— groups;

$R^3$ is hydrogen, halogen, cyano, an alkyl, alkoxy, alkoxycarbonyl or alkanoyloxy groups, the alkyl, alkoxy, alkoxycarbonyl, or alkanoyloxy group being unsubstituted or substituted with one or more of methoxy, cyano or halogen; and each of $X^1$, $X^2$ and $X^3$ independently is hydrogen, halogen, cyano or lower alkyl, whereby rings B and D can be the same or different when either or both of m and n is 2 wherein the compound of formula I is in a cross-linked state; and (c) means for applying an electrical potential to the plate means.

19. The electro-optical cell according to claim 18 wherein (b) further contains one or more compounds selected from the group consisting of the formulae

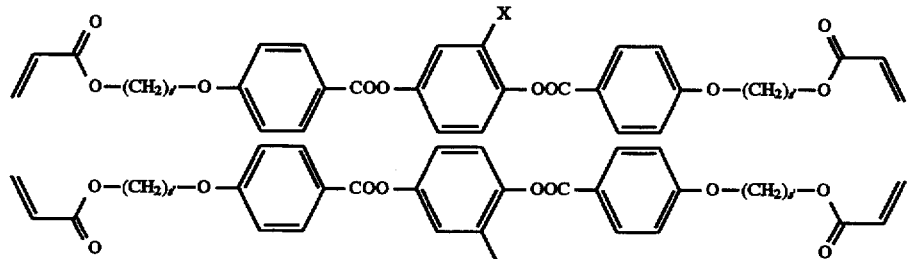

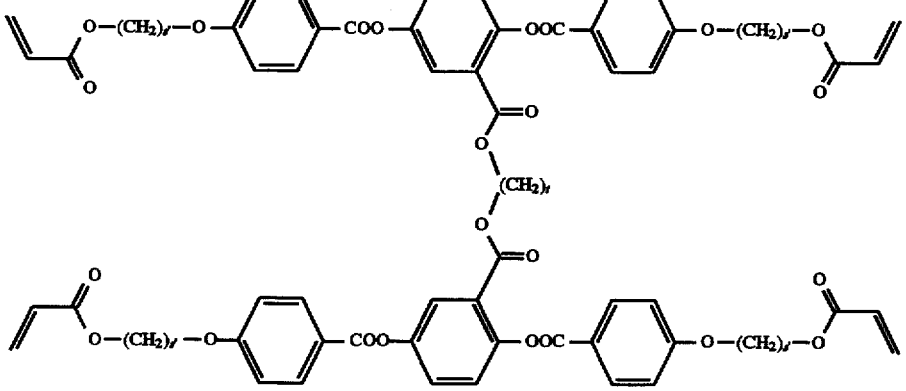

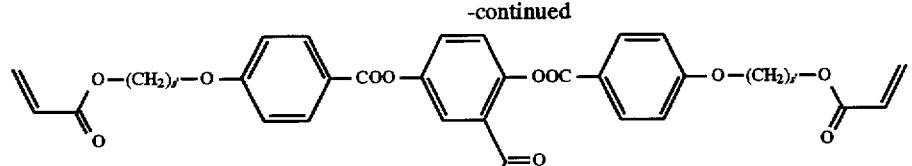
IV
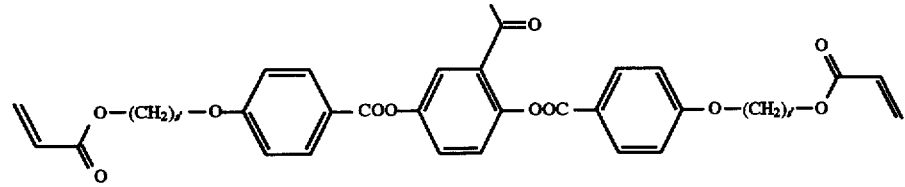
V
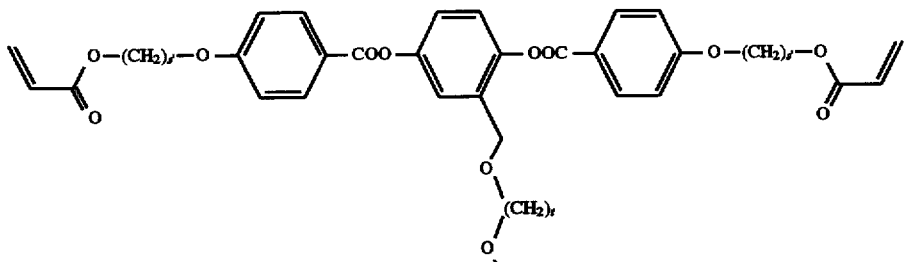
VI
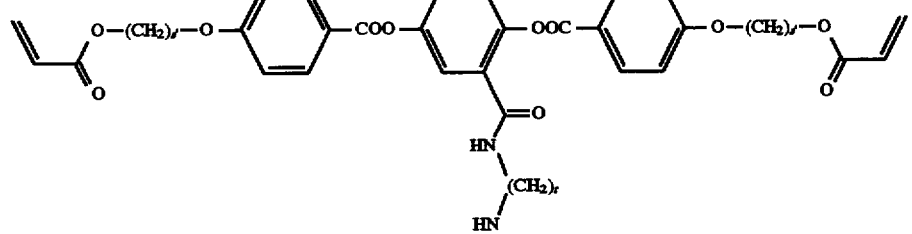
VII
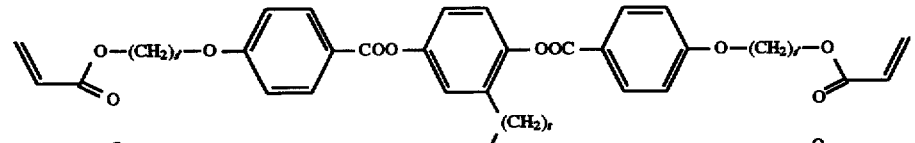
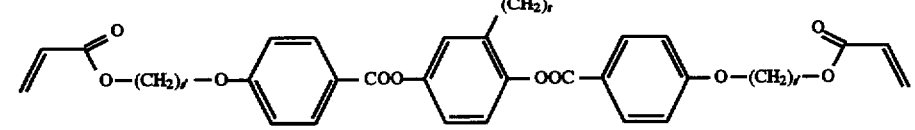

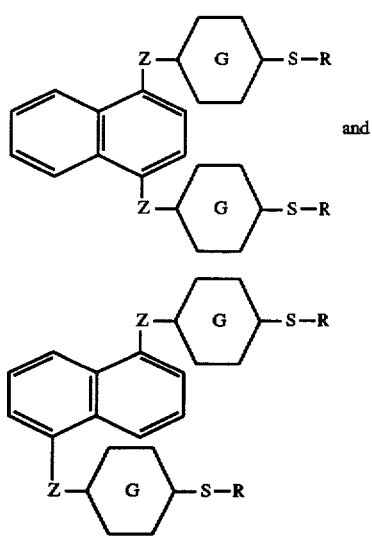
and
wherein
X is hydrogen, fluorine, chlorine, bromine or methyl;
s' is a whole number of 3 to 12; and
t is a whole number of 2 to 12;
Z is —OCH$_2$— or —OOC—;
G is 1,4-phenylene or 2- or 3-fluoro-1,4-phenylene;
S is —(CH$_2$)$_{s'}$— or —(CH$_2$)$_s$O—; and
R is CH$_2$=CH—COO—, CH$_2$=C(CH$_3$)—COO—, CH$_2$=CH—O— or H$_2$C—CH—.
                                                        \\O/
* * * * *

UNITED STATES PATENT AND TRADEMARK OFFICE
CERTIFICATE OF CORRECTION

PATENT NO. : 5,800,733
DATED : September 1, 1998
INVENTOR(S) : Stephen KELLY

It is certified that error appears in the above-identified patent and that said Letters Patent is hereby corrected as shown below:

In claim 18, column 58, line 21, change "$X^{2 \text{ and } X3}$" to --$X^2$ and $X^3$--.

Signed and Sealed this

Sixth Day of July, 1999

Attest:

Q. TODD DICKINSON

*Attesting Officer*     *Acting Commissioner of Patents and Trademarks*